United States Patent
Li et al.

(10) Patent No.: US 11,833,219 B2
(45) Date of Patent: Dec. 5, 2023

(54) METHOD FOR PRODUCING ANTIBODY-DRUG CONJUGATE INTERMEDIATE BY ADDITION OF ACID AND USE THEREOF

(71) Applicant: MABPLEX INTERNATIONAL CO., LTD., China (Shandong) Pilot Free Trade Zone (CN)

(72) Inventors: Lele Li, Shandong (CN); Changjiang Huang, Shandong (CN); Youxiang Sun, Shandong (CN)

(73) Assignee: MABPLEX INTERNATIONAL CO., LTD., China (Shandong) Pilot Free Trade Zone (CN)

( * ) Notice: Subject to any disclaimer, the term of this patent is extended or adjusted under 35 U.S.C. 154(b) by 586 days.

(21) Appl. No.: 16/650,273

(22) PCT Filed: Nov. 14, 2019

(86) PCT No.: PCT/CN2019/118446
§ 371 (c)(1),
(2) Date: Mar. 24, 2020

(87) PCT Pub. No.: WO2021/056754
PCT Pub. Date: Apr. 1, 2021

(65) Prior Publication Data
US 2021/0393733 A1    Dec. 23, 2021

(30) Foreign Application Priority Data
Sep. 29, 2019   (CN) .......................... 201910934570.0

(51) Int. Cl.
*A61K 47/68*   (2017.01)
(52) U.S. Cl.
CPC ...... *A61K 47/6817* (2017.08); *A61K 47/6811* (2017.08)
(58) Field of Classification Search
CPC ......... A61P 35/00; C07K 7/06; C07K 5/0205; A61K 47/6817; A61K 47/6811; A61K 47/6889; A61K 38/05; A61K 47/18; A61K 47/22; A61K 47/545
See application file for complete search history.

(56) References Cited

U.S. PATENT DOCUMENTS

| | | | |
|---|---|---|---|
| 9,539,342 B2 * | 1/2017 | Pettit | ........................ A61P 43/00 |
| 2015/0152190 A1 | 6/2015 | Barnett et al. | |
| 2015/0157736 A1 | 6/2015 | Rabuka et al. | |
| 2017/0121413 A1 | 5/2017 | Nittoli et al. | |

FOREIGN PATENT DOCUMENTS

| | | | | |
|---|---|---|---|---|
| CN | 105744935 | | 7/2016 | |
| CN | 106573074 | | 4/2017 | |
| CN | 108727466 | | 11/2018 | |
| CN | 109824759 | | 5/2019 | |
| WO | WO-2014065661 A1 | * | 5/2014 | ............. A61K 47/61 |
| WO | WO-2015189791 A1 | * | 12/2015 | ............. A61K 38/00 |
| WO | WO 2016/064749 | | 4/2016 | |

OTHER PUBLICATIONS

Hwang D et al. Site-Selective Antibody Functionalization via Orthogonally Reactive Arginine and Lysine Residues. Cell Chem Bio. 2019 26, 1229-1239 (Year: 2019).*
Carpino LA and El-Faham A. Effect of Tertiary Biases on O-Benzotriazolyluronium Salt-Induced Peptide Segment Coupling. J. Org. Chem. 1994 59, 695-698 (Year: 1994).*
Ishihara K. Rational design of dynamic ammonium salt catalysts towards more flexible and selective function. Proc Jpn Acad Ser B Phys Biol Sci. Oct. 2009; 85(8): 290-313 (Year: 2009).*
Doronina SV et al. Enhanced Activity of Monomethylauristatin F through Monoclonal Antibody Delivery: Effects of Linker Technology on Efficacy and Toxicity Bioconjugate Chem. 2006, 17, 1, 114-124. (Year: 2006).*
Magtaan JK et al. Regeneration of aged DMF for use in solid-phase peptide synthesis. J Pep Sci. 2019 25:e3139 1-9. (Year: 2019).*
Clark J Enthalpy change of neutralisation Internet Archive https://www.chemguide.co.uk/physical/energetics/neutralisation.html pp. 1-3, Sep. 25, 2018 (Year: 2018).*
Jain N et al. Current ADC Linker Chemistry. Pharm Res. 2015; 32(11): 3526-3540 (Year: 2015).*
Aubrey et al., "Site-Specific Conjugation of Auristatins onto Engineered scFv Using Second Generation Maleimide to Target HER2-positive Breast Cancer in Vitro," *BioConjugate Chemistry*, 29:3516-3521, 2018.
Aubrey et al., "Site-Specific Conjugation of Auristatins onto Engineered scFv Using Second Generation Maleimide to Target HER2-positive Breast Cancer in Vitro—Supporting information," BioConjugate Chemistry, 29:3516-3521, 20182018.
Bryden et al., "Impact of cathepsin B-sensitive triggers and hydrophilic linker on in vitro efficacy of novel site-specific antibody—drug conjugates", *Org.Biomol Chem*, 16:1882-1889, 2018.
Dias et al., "Synthesis and Biological Evaluation of RGD and isoDGR-Monomethyl Auristatin Conjugates Targeting Integrin $a_v\beta_3$", *ChemMedChem*, 14:938-942, 2019.

(Continued)

*Primary Examiner* — Adam Weidner
*Assistant Examiner* — John J Skoko, III
(74) *Attorney, Agent, or Firm* — Parker Highlander PLLC

(57) ABSTRACT

Provided is a method for producing an antibody-drug conjugate intermediate by addition of acid. An acid additive is used to convert the monomethyl auristatin derivative into a salt thereof to participate in the reaction. The addition of the acid additive can significantly improve the yield of the final product. In addition, the low price of the acid additive greatly reduces the production cost of the final ADC product. Moreover, the method of the present invention adopts a one-step preparation process, in addition to a higher yield of the final product, not only reducing the cost of the consumables, labor, equipment, site, raw materials and the like in the production, but also greatly reducing the production of the waste liquid, and thus reducing production costs and improving production efficiency, and making the method suitable for industrial large-scale production.

5 Claims, 3 Drawing Sheets

(56) References Cited

OTHER PUBLICATIONS

Dias et al., "Synthesis and Biological Evaluation of RGD and isoDGR-Monomethyl Auristatin Conjugates Targeting Integrin $a_v\beta_3$—Supporting Information", *ChemMedChem*, 14:938-942, 2019.

Hwang et al., "Site-Selective Antibody Functionalization via Orthogonally Reactive Arginine and Lysine Resides", Cell Chemical Biology, 16:1-11, 2019.

Office Communication issued in correspondence Japanese Application No. 2021-525571 dated May 24, 2022 {English translation}.

Supplemental Search Report issued in European Application No. 19941775.9, dated Mar. 29, 2022.

English translation of PCT International Search Report and Written Opinion issued in International Application No. PCT/CN2019/118446, dated Jun. 23, 2020.

Behrens et al., "Antibody-Drug Conjugates (ADCs) Derived From Interchain Cysteine Cross-Linking Demonstrate Improved Homogeneity and Other Pharmacological Properties Over Conventional Heterogeneous ADCs," *Mol. Pharmaceuticals*, 12(11)3986-3998, 2015.

Doronina et al., "Enhanced Activity of Monomethylauristatin F through Monoclonal Antibody Delivery: Effects of Linker Technology on Efficacy and Toxicity," *Bioconjugate Chem.*, 17:114-1214, 2006.

Office Communication issued in Australian Patent Application No. 2019341067, dated Oct. 9, 2020.

\* cited by examiner

METHOD FOR PRODUCING ANTIBODY-DRUG CONJUGATE INTERMEDIATE BY ADDITION OF ACID AND USE THEREOF

This application is a national phase application under 35 U.S.C. § 371 of International Application No. PCT/CN2019/118446, filed Nov. 14, 2019, which claims priority to Chinese Patent Application No. 201910934570.0, filed Sep. 29, 2019, the disclosures of which are hereby incorporated by reference in their entirety.

FIELD OF THE INVENTION

The present invention relates to the field of antibody-drug conjugates, in particular to a method for producing an antibody-drug conjugate intermediate and its use in the production of antibody-drug conjugates.

BACKGROUND OF THE INVENTION

Antibody-Drug Conjugate (ADC), as a new type of biological missile, achieves an advantageous combination of the targeting effect of monoclonal antibodies and the cytotoxic effect of small molecule drugs, and has now become one of the fastest developing fields in tumor targeted therapy. The three components (antibodies, cytotoxins and linkers) of ADC together constitute a targeted drug delivery system, in which the antibodies provide the targeting effect, the linkers ensure the stability of the ADC in the blood transport process, and the toxins exert killing effect on cancer cells after reaching the target.

Currently, auristatins or maytansinoids are the two most widely used mitotic inhibitors in ADC development. They can bind to tubulin near the vinblastine binding site, causing cell cycle arrest at G2/M phase and subsequent cell apoptosis. This cell killing mechanism is very effective in rapidly proliferating cells, but non-dividing and static cells may be less sensitive to drug effects, and thus have drug resistance. Because tumor cells divide faster than most normal cells, anti-mitotic drugs are particularly effective for cancer cells. Due to this inherent selectivity, tubulin inhibitors with high efficacy, such as maytansin and auristatin, have been successfully used as clinically approved ADC drugs (brentuximabvedotin and trastuzumabemtansine, etc.).

Dolastatin is a class of linear polypeptide compounds with high cytotoxicity found in *Dolabella scapula* in the Indian Ocean, and such cytotoxic drugs can significantly inhibit formation and polymerization of tubulin. However, Dolastatin 10, when used alone, has problems such as large toxic side effects, poor pharmacokinetic properties, and narrow therapeutic window, limiting its development. Miyazaki et al. found that monomethyl auristatin D (MMAD) with a secondary amine at the N-terminus has comparable toxicity to Dolastatin10, so such N-monomethyl substituted Dolastatin derivative is termed auristatin. Such compound can be effectively connected to the linker, and based on this, a new generation of high-efficiency ADC has been generated. At present, the warhead molecules commonly used in ADC research and development are auristatin compounds MMAE and MMAF (Hu Xinyue, Li Yanping, Li Zhuorong. Progress in the research of warhead molecules for antibody-drug conjugates [J]. China Medical Biotechnology, 2017 (6): 549-555).

MMAF (Monomethyl auristatin F) is a derivative of dolastatin10 (D10), which can inhibit cell mitosis and has strong antitumor activity. At present, MMAF is used as cytotoxic molecule in various ADC products in clinical stage, and is the most used monomethyl auristatin derivative in ADC. However, these small molecule drugs are expensive.

The market price of MMAF is close to 5,000 yuan per 10 mg, while the market price of Mc-MMAF intermediate used for coupling to antibodies is close to 6000 yuan per 1 mg. The price from MMAF to Mc-MMAF intermediate has increased more than ten times (the prices of MMAF and Mc-MMAF can be found at the following URL: world-wide-web at medchemexpress.cn/mmaf-hydrochloride-.html?src=360-product, world-wide-web at medchemexpress.cn/McMMAF.html). The high price of ADC intermediates is a main reason for the high cost of related ADC production.

An important reason for the increasing price of related ADC intermediates (linker-drug covalent conjugates) relative to the corresponding cytotoxic molecules is the low yield of the antibody-drug conjugate intermediates during the preparation process. Therefore, increasing the yield of related ADC intermediates can effectively control the cost of ADC drugs on a large scale.

The structure of Mc-MMAF is shown below:

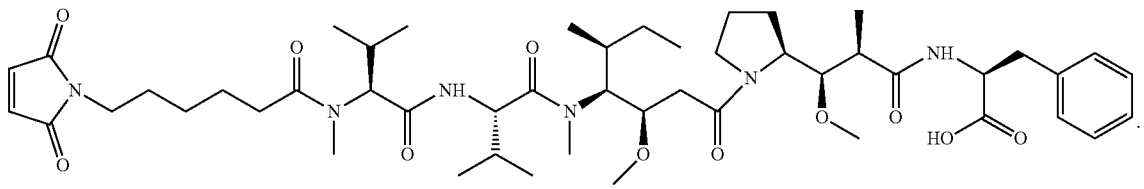 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)C(=O)CCCCCN1C(=O)C=CC1=O)C(C)C]

The structure of Mc-MMAE is shown below:

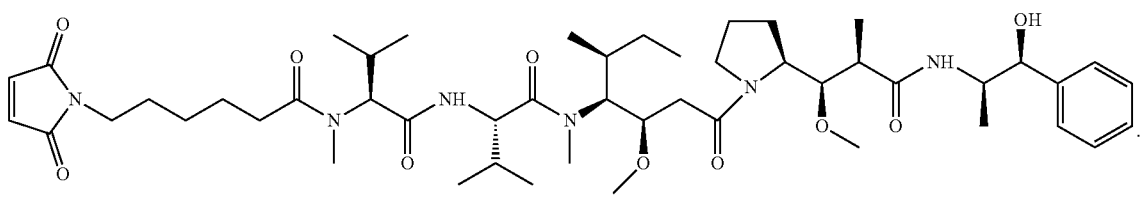 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)CCCCCN1C(=O)C=CC1=O)C(C)C]

The Mc-MMAD structure is shown below:

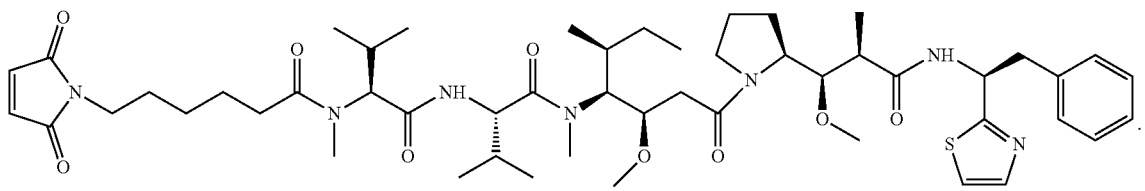 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)C(=O)CCCCCN1C(=O)C=CC1=O)C(C)C]

Chinese Patent Publication No. CN1938046A discloses two methods for preparing Mc-MMAF (Pages 206-207 of the specification and pages 207-208 of the specification, respectively), one of which is the synthesis of Mc-MMAF using tert-butyl ester, and the other is the synthesis of Mc-MMAF using dimethoxybenzyl esters. The reaction scheme of the two methods are as follows:

(1) Synthesis of Mc-MMAF Using Tert-Butyl Ester

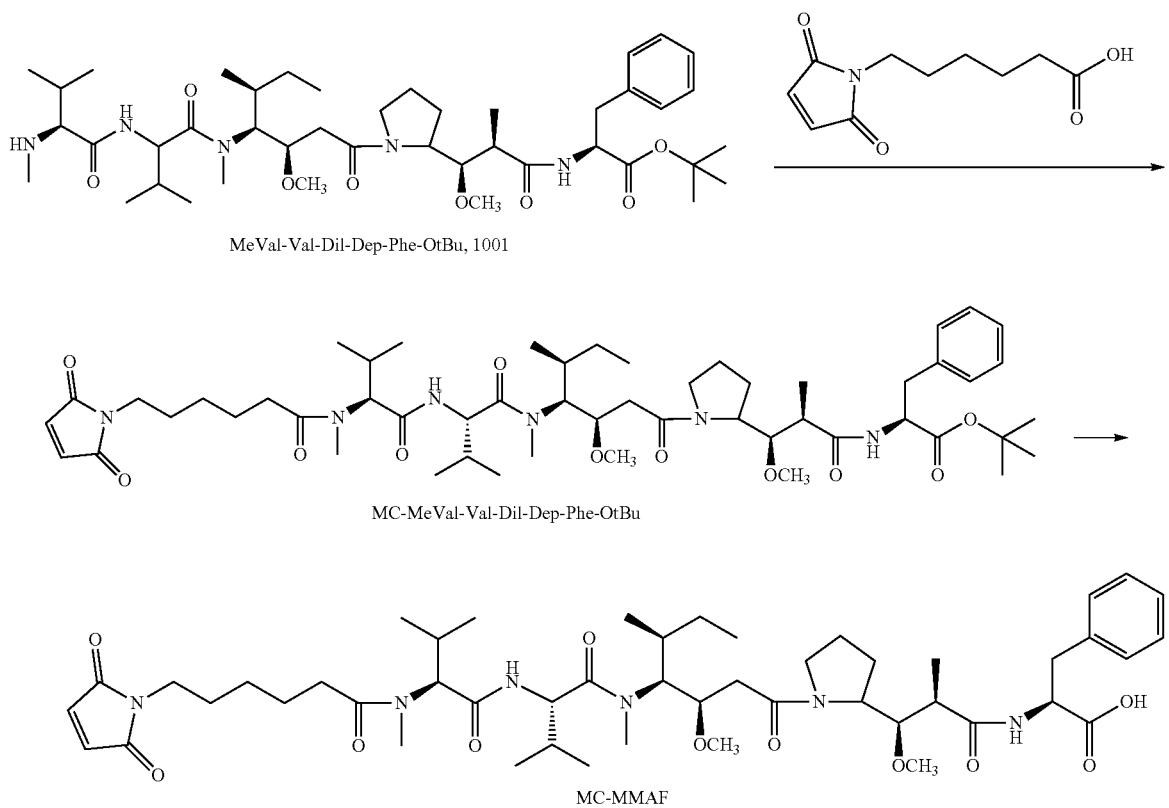

(2) Synthesis of Mc-MMAF Using Dimethoxybenzyl Ester

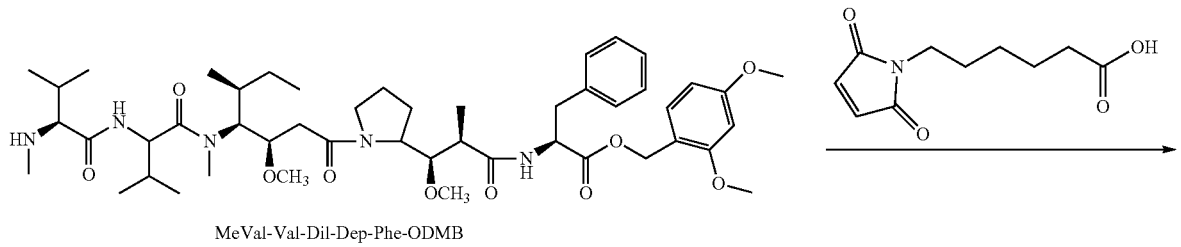

-continued

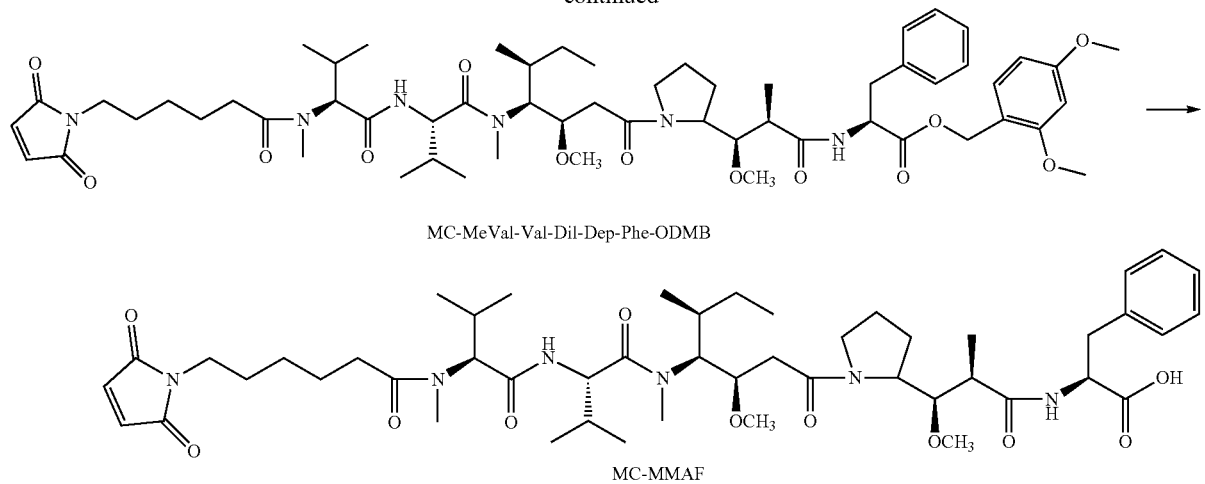

MC-MeVal-Val-Dil-Dep-Phe-ODMB

MC-MMAF

Both schemes use two-step synthesis processes. The synthesis of Mc-MMAF using tert-butyl ester is performed by the initial synthesis of Mc-MMAF-OtBu (that is, Mc-MeVal-Val-Dil-Dap-Phe-OtBu), and following by deesterification with trifluoroacetic acid to obtain Mc-MMAF (total yield below 60%). The synthesis of Mc-MMAF using dimethoxybenzyl ester is performed by the initial synthesis of Mc-MMAF-ODMB (that is, Mc-MeVal-Val-Dil-Dap-Phe-ODMB), and following by deesterification with trifluoroacetic acid to obtain Mc-MMAF. The disadvantages of the two-step synthesis processes are that, the yield in the first step is 57%, the yield in the second step is 73%, and the total yield is only 42%; and MMAF-ODMB is not easy to be obtained.

Chinese Patent No. CN109824759A also discloses a method for producing Mc-MMAF (line [0009] on page 2 of the description) by directly reacting Mc with MMAF. Its reaction scheme is as follows:

The N-terminal valine of MMAF in this scheme has a methyl group on the N, which has a large steric hindrance, causing the reaction rate of attaching maleimido-hexanoic acid (Mc-hex-Acid) to MMAF slower. This scheme is used for the synthesis of MC-MMAF less than 1 g, and has a yield less than 50%, and high pressure reverse phase preparation is used to remove heterogeneous impurities.

SUMMARY OF THE INVENTION

The present invention provides a method for producing an antibody-drug conjugate intermediate by addition of acid. The technical solutions of the present invention are as follows.

A method for producing an antibody-drug conjugate intermediate by addition of acid, wherein the reaction scheme of the method is as follows:

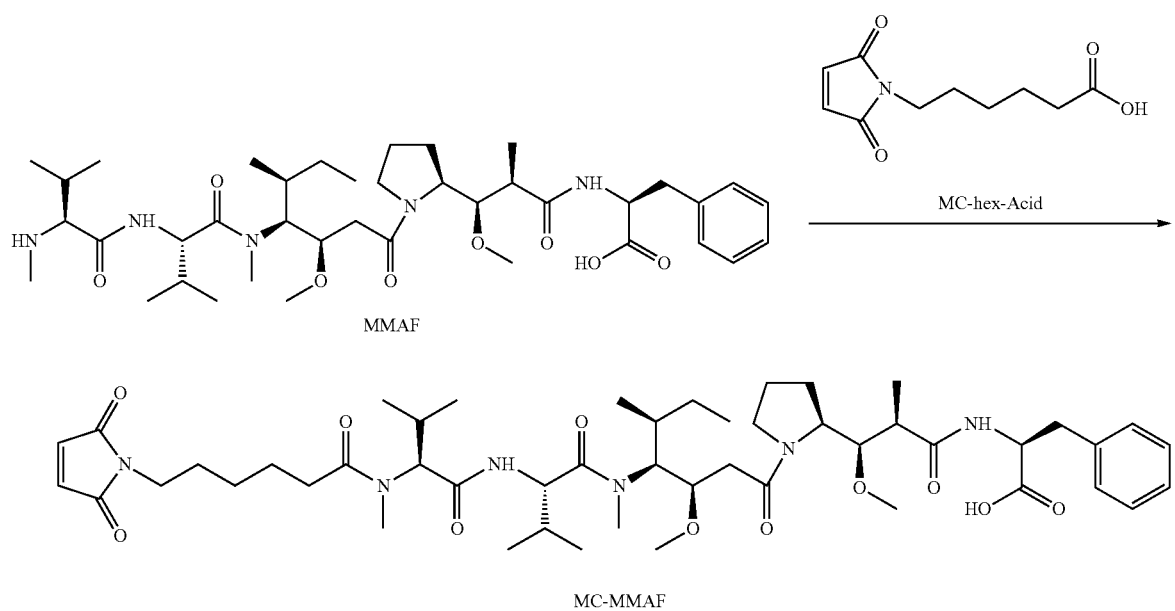

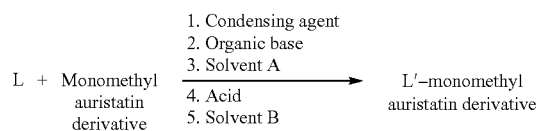

wherein
L is a linking group containing an acyl;
L' is the residue of the linking group covalently attached to the monomethyl auristatin derivative;
solvent A and solvent B are polar or non-polar solvents; and
the method comprises the following steps:
1) dissolving the linking group L, the condensing agent, and the organic base in the solvent A to obtain solution 1;
2) dissolving the monomethyl auristatin derivative and the acid in the solvent B to obtain solution 2; and
3) adding the solution 1 into the solution 2 to obtain the L'-monomethyl auristatin derivative via the condensation reaction between L and the monomethyl auristatin derivative;

wherein the molar amount of the organic base used in step 1) is greater than the molar amount of all free carboxyl group in the reaction system of step 3).

Further, the acid is one or more selected from trifluoroacetic acid and sulfonic acid.

Further, the monomethyl auristatin derivative includes MMAF, MMAE, and MMAD.

Further, the reaction scheme of the method is as follows:

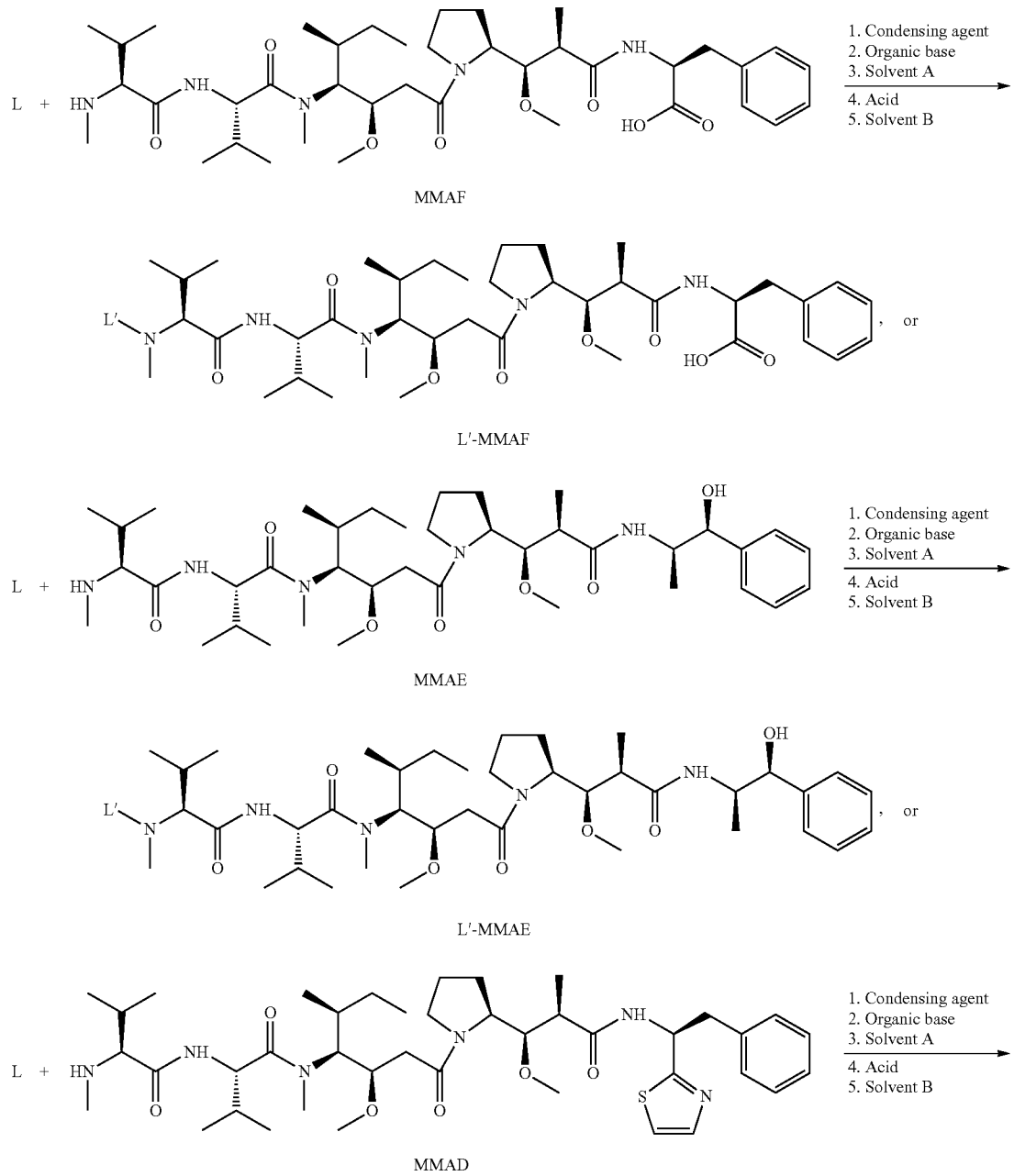

-continued

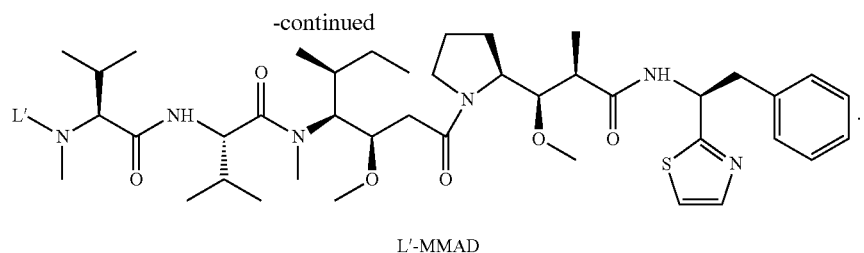

L′-MMAD

Further, the condensing agent is one or more selected from DCC, EDCI, DIC, HATU, HBTU, HBPIPU, HBPyU, HCTU, HDMA, TATU, TBTU, TCTU, TCFH, TDBTU, TFFH, BTFFH, PyBOP, PyClOP, PyAOP, PyCIU, DEPBT and EEDQ; preferably, the condensing agent is HATU.

Further, the organic base is one or more selected from N,N-diisopropylethylamine, triethylamine, pyridine, dimethylaminopyridine, triethylenediamine, N-methylmorpholine, 1,8-diazabicyclo[5.4.0]-7-undecene, N-methylimidazole, quinuclidine, and trimethylpyridine; preferably, the organic base is selected from N,N-diisopropylethylamine and triethylamine.

Further, the solvent A and the solvent B are each independently selected from DMF, DMA, NMP, methylene chloride, carbon tetrachloride, DMSO, chloroform, tetrahydrofuran, 1,4-dioxane, hexamethylphosphoryl triamide, N,N-dimethylpropyleneurea, ethylene glycol dimethyl ether and a mixture thereof, wherein the solvent A and the solvent B may be the same or different; preferably, the solvent A and the solvent B are selected from DMF, DMA and DMSO.

Furthermore, the sulfonic acid is one or more selected from p-toluenesulfonic acid, benzenesulfinic acid, trifluoromethanesulfonic acid, (−)-10-camphorsulfonic acid, (+)-10-camphorsulfonic acid and methanesulfonic acid; preferably, the p-toluenesulfonic acid is p-toluenesulfonic acid monohydrate.

Preferably, L is any linking group containing an acyl, having the structure shown in formula (I):

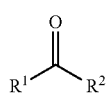

(I)

wherein:
$R^1$ is selected from

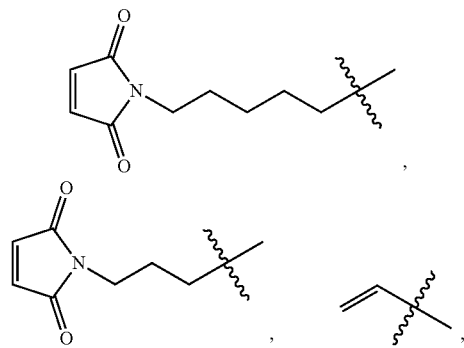

-continued

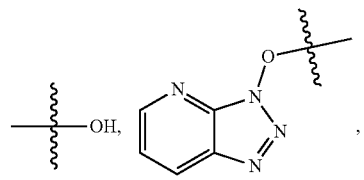

$R^2$ is selected from

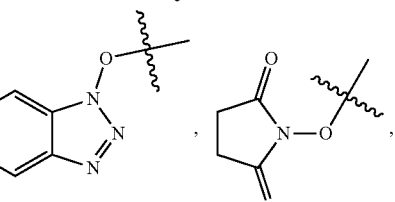

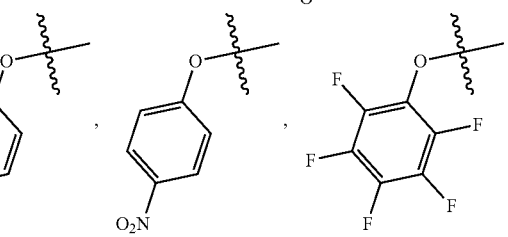

and salts thereof.

More preferably, L is selected from the following structures:

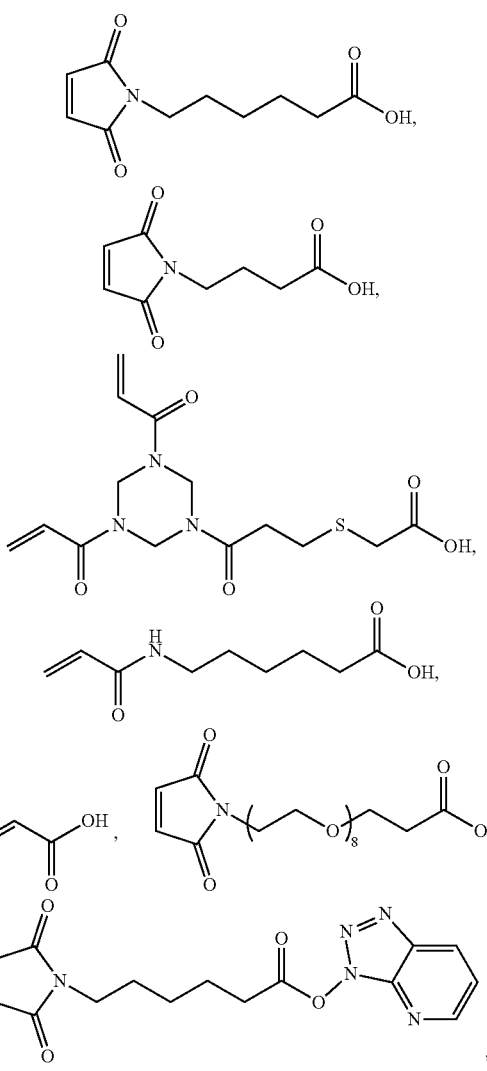
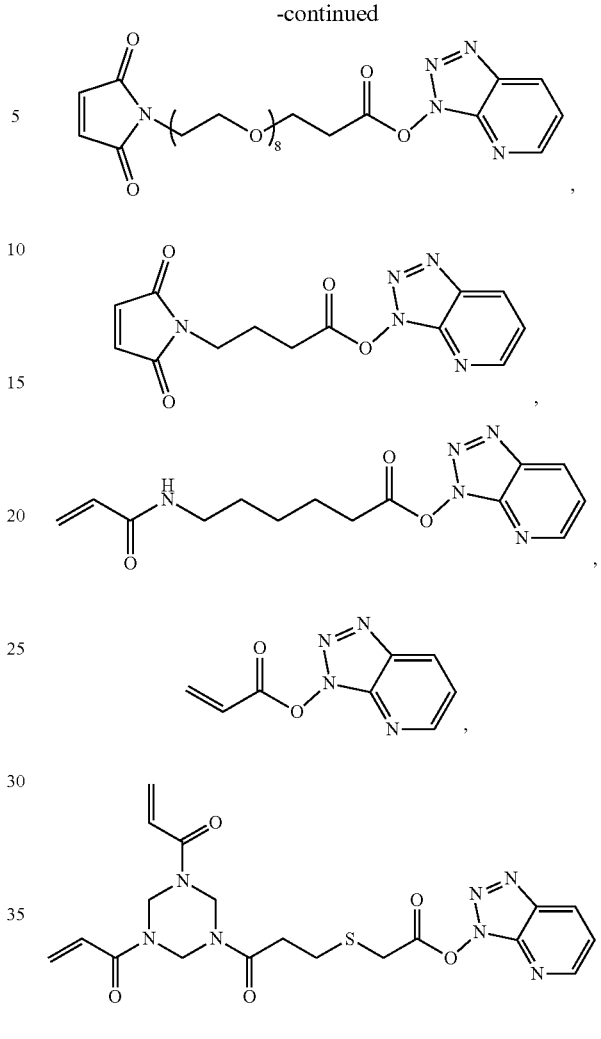
More preferably, L'-MMAF is selected from the following structures:
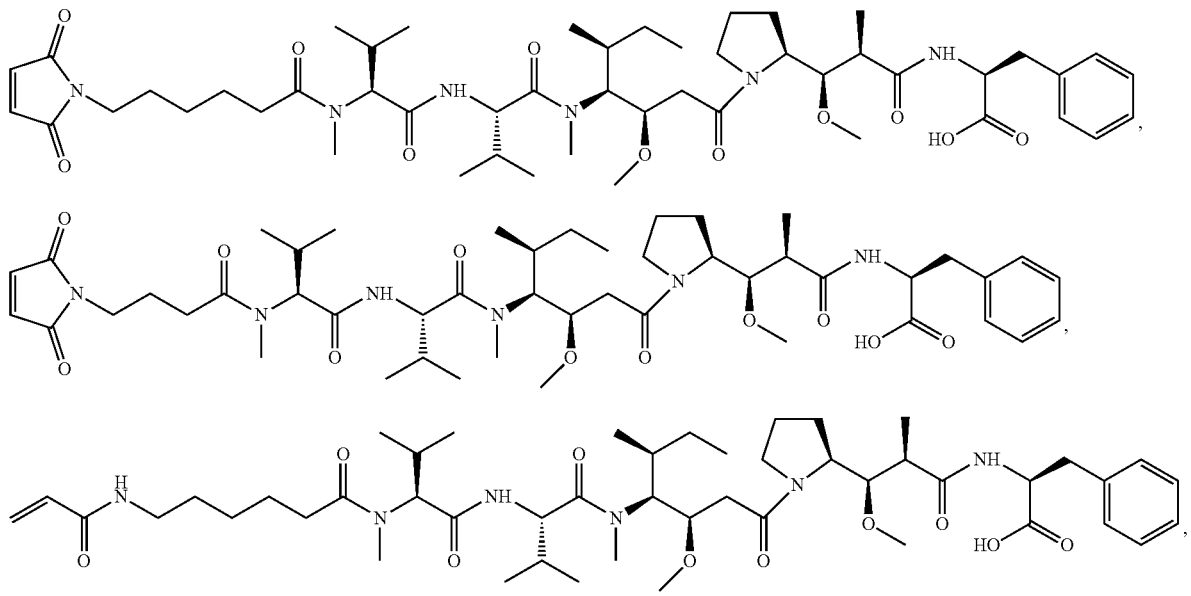

-continued

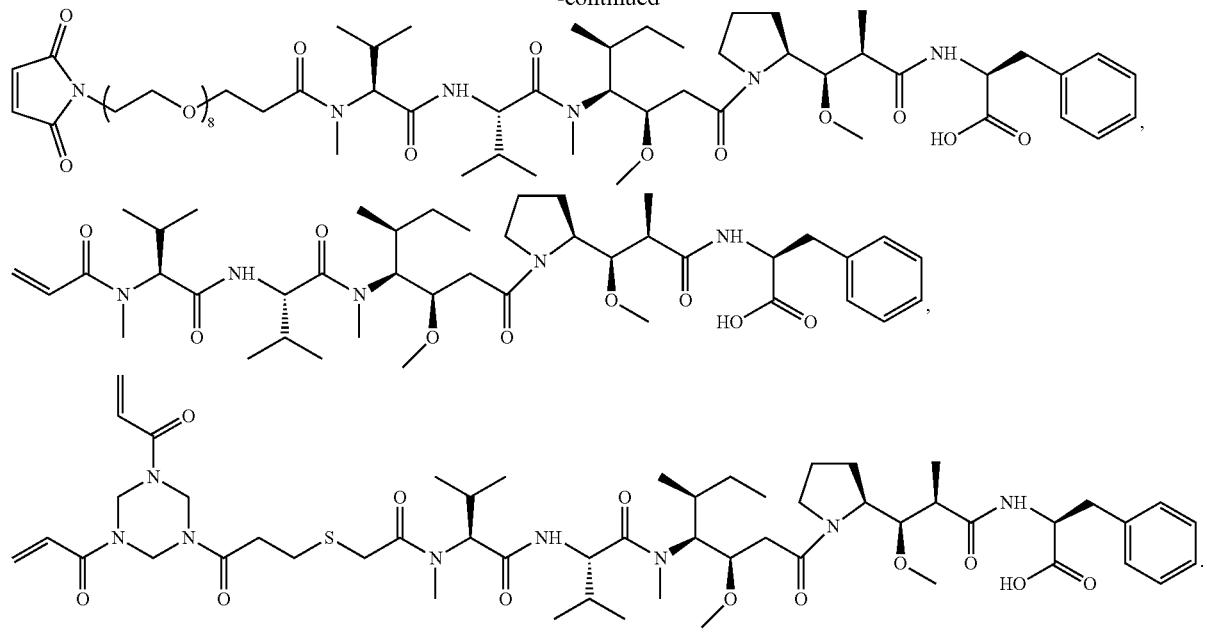

Furthermore, the molar ratio of the acid to the corresponding monomethyl auristatin derivative is preferably greater than or equal to 1, or greater than or equal to 2.

Furthermore, the solution 1 is added into solution 2 evenly, preferably, by dropwise addition.

The present invention also provides use of the method according to any one of the foregoing in the production of an antibody-drug conjugate.

The method for producing an antibody-drug conjugate intermediate (specifically, a linking group-MMAF covalent conjugate) by addition of acid provided in the present invention is a method of adding an acid additive to convert MMAF into a salt to participate in the reaction, based on the traditional preparation method (the preparation method disclosed in line [0009] on page 2 of the description of Chinese Patent Publication No. CN109824759A). After a series of reactions, we surprisingly find that the addition of the acid can significantly improve the yield of the final product. In addition, the low price of the acid (negligible relative to MMAF) can greatly reduce the production cost of the final ADC product. In addition, compared with the two-step process disclosed in Patent Publication No. CN109824759A, the method provided by the present invention adopts a one-step preparation process, in addition to a higher yield of the final product, which not only reduces the cost of the consumables, labor, equipment, site, raw materials and the like in the production, but also greatly reduces the production of the waste liquid, and thus reduces production costs and improves production efficiency, and is suitable for industrial large-scale production.

DETAILED DESCRIPTION OF THE INVENTION

Abbreviation

Figure 1:
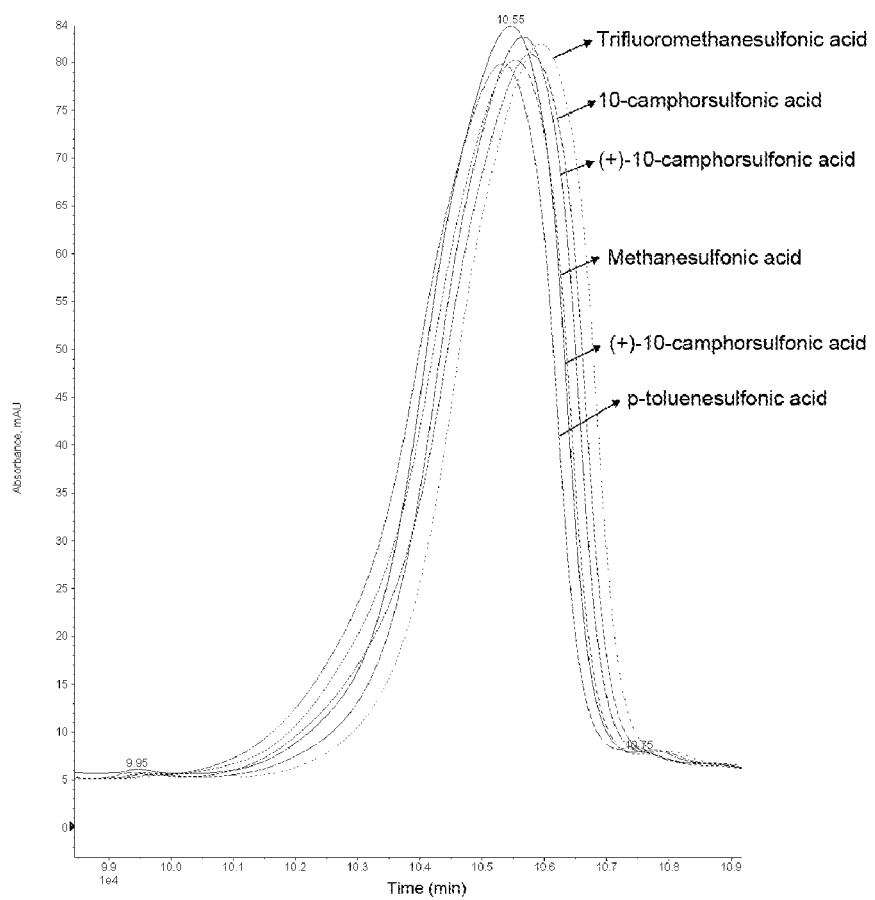
FIG. 1 is a liquid chromatogram of the products obtained by adding various sulfonic acid additives in Example 2 of the present invention.

Unless otherwise stated, all abbreviations used in the present invention have the same meaning as understood by those of ordinary skill in the art. As used in the present invention, the common abbreviations and their definitions are as follows:

| Abbreviation | Definition |
| --- | --- |
| DCC | N,N'-dicyclohexylcarbodiimide |
| EDCI | 1-(3-dimethylaminopropyl)-3-ethylcarbodiimide hydrochloride |
| DIC | N,N'-Diisopropylcarbodiimide |
| HATU | 2-(7-azobenzotriazole)-N,N,N',N'-tetramethyluronium hexafluorophosphate |
| HBTU | O-benzotriazole-N,N,N',N'-tetramethyluronium hexafluorophosphate |
| HBPIPU | (Benzotriazol-1-yloxy)dipiperidinocarbenium hexafluorophosphate |
| HBPyU | O-(benzotriazol-1-yl)-N,N,N',N'-dipyrrolidinocarbenium hexafluorophosphate |
| HCTU | 6-chlorobenzotriazol-1,1,3,3-tetramethyluronium hexafluorophosphate |
| HDMA | 1-[(dimethylamino)(morpholino)methylene]-1H-[1,2,3]triazolo[4,5-b]pyridine-1-ium 3-oxide hexafluorophosphate |
| TATU | O-(7-azabenzotriazole-yl)-N,N,N',N'-tetramethyluronium tetrafluoroborate |
| TBTU | O-benzotriazole-N,N,N',N'-tetramethyluronium tetrafluoroborate |
| TCTU | O-(6-chloro-1H-benzotriazol-1-yl)-N,N,N',N'-tetramethylmonium tetrafluoroborate |

-continued

| Abbreviation | Definition |
|---|---|
| TCFH | N,N,N',N'-tetramethylchloroformamidinium hexafluorophosphate |
| TDBTU | N,N,N',N'-tetramethyl-O-(3,4-dihydro-4-oxo-1,2,3-benzotriazin-3-yl)uronium tetrafluoroborate |
| TFFH | fluoro-N,N,N',N'-tetramethylformamidinium hexafluorophosphate |
| BTFFH | N,N,N',N'-bis(tetramethylene)fonnamidinium hexafluorophosphate |
| TSTU | 2-succinimido-1,1,3,3-tetramethyluronium tetrafluoroborate |
| PyBOP | 1H-benzotriazol-1-yloxytripyrrolidinophosphonium Hexafluorophosphate |
| PyClOP | Chlorotri(1-pyrrolidinyl)phosphonium hexafluorophosphate |
| PyAOP | (3-hydroxy-3H-1,2,3-triazolo[4,5-b]pyridinato-O)tri-1-pyrrolidinylphosphonium hexafluorophosphate |
| PyCIU | 1-(chloro-1-pyrrolidinylmethylene)pyrrolidinium hexafluorophosphate |
| DEPBT | 3-(diethoxyphosphoryloxy)-1,2,3-benzotrizin-4(3H)-one |
| EEDQ | 2-ethoxy-1-ethoxycarbonyl-1,2-dihydroquinoline |
| Mc | Maleimidohexanoyl |
| MMAF | Monomethylauristatin F |
| DMF | Dimethylfonnamide |
| DMA | Dimethylacetamide |
| NMP | NMP |
| DMSO | Dimethyl sulfoxide |

Definition

Various terms related to various aspects of the specification are used throughout the specification and claims. Unless otherwise indicated, such terms are given their ordinary meaning in the art. Other specifically defined terms should be understood in a manner consistent with the definitions provided herein.

As used herein, the terms "a" and "an" and "the" are used in accordance with standard practice and mean one or more, unless the context indicates otherwise. Thus, for example, reference to "an antibody-drug conjugate" includes a combination of two or more antibody-drug conjugates and the like.

It should be understood that wherever an aspect is described herein with the word "comprising", it also provides similar aspects described with "consisting of" and/or "substantially consisting of".

Although the numerical ranges and parameter approximations shown in the broad scope of the present invention, the numerical values shown in the specific examples are described as accurately as possible. However, any numerical value inherently must contain a certain amount of error, which is caused by the standard deviation present in their respective measurements. In addition, all ranges disclosed herein are understood to cover any and all sub-ranges contained therein. For example, a recorded range of "1 to 10" should be considered to include any and all sub-ranges between a minimum of 1 and a maximum of 10 (inclusive); that is, all sub-ranges beginning with a minimum of 1 or greater, such as 1 to 6.1, and sub-ranges ending with a maximum of 10 or less, such as 5.5 to 10. In addition, any reference referred to as "incorporated herein" is to be understood as being incorporated in its entirety.

As used in the present invention,

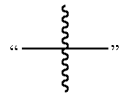

means that the group containing

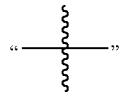

is connected to other groups through the chemical bond here.

The term "linking group" used in the present invention refers to a bifunctional or multifunctional molecule, which can react with a protein/antibody molecule and MMAF, respectively, and thus function as a "bridge" to link the protein/antibody to MMAF. The linking group used in the present invention specifically refers to a group containing an acyl in the structure.

The term "antibody-drug conjugate intermediate" in the present invention refers to a covalent conjugate of a linking group and MMAF.

EXAMPLE

The following further describes the present invention in combination with specific examples. It should be understood that these examples are only used to illustrate the present invention and not to limit the scope of the present invention. The experimental methods without specific conditions in the following examples are generally performed under conventional conditions or conditions recommended by the manufacturer. The reagents without specific sources are conventional reagents purchased on the market. Unless otherwise stated, all percentages, ratios, proportions, or parts are by weight.

The units in weight-volume percentage in the present invention are well known to those skilled in the art, and for example, refer to the weight of a solute in 100 ml of a solution.

Unless otherwise defined, all specialties and sciences used herein are used in the same sense as that familiar to those skilled in the art. In addition, any method or material similar or equal to the content described can be used in the method of the present invention. The preferred embodiments and materials described herein are for illustration purposes only.

Example 1

Mc-MMAF Preparation Method 1 (without Adding Acid)

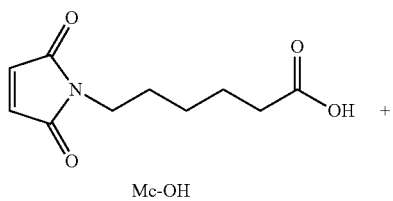

Mc-OH

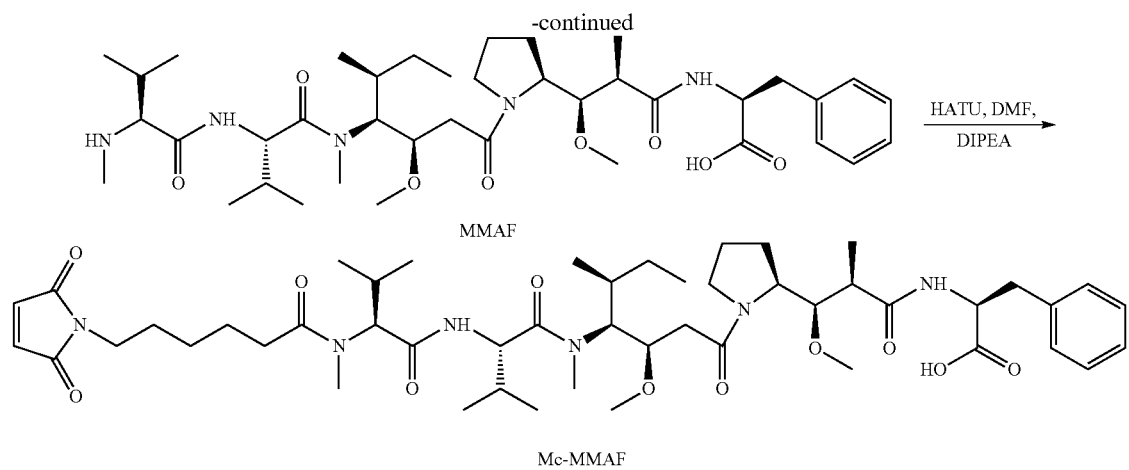

MMAF

Mc-MMAF 84.6 mg of Mc-OH and 144.6 mg of HATU were weighed and added into a 50 mL round bottom flask, then 5 mL of N,N-dimethylformamide was added into the round bottom flask using a 5 mL syringe, and then 165.4 μL of N,N-diisopropylethylamine was added into the flask using a 200 μL pipettor. The flask was placed on a magnetic stirrer, and after adding a stir bar, stirring was performed at room temperature for 0.5 h. 146.4 mg of MMAF was weighed and added into a 25 mL round bottom flask, and then 10 mL of N,N-dimethylformamide was added into the flask using a 10 mL syringe. After adding a stir bar, the flask was placed on a magnetic stirrer and stirring was performed in an ice bath. Under the ice bath condition, the Mc-OH system was added into the MMAF solution using a 5 mL plastic dropper. The ice bath was removed from the magnetic stirrer, and the mixture was stirred for 1 h. Then, the reaction was stopped, 10 μL of sample was taken and added into a 1.5 mL centrifuge tube using a 10 μL pipettor, and then 1 mL of acetonitrile was added into the centrifuge tube using a 1 mL pipettor. The sample was taken by a 1 ml syringe and passed through an organic phase needle filter, and then loaded for LC-MS to check the reaction.

After the reaction was completed, the solvent was spin-dried with a rotary evaporator, and 5 mL of acetonitrile was added. The sample was taken using a 5 mL syringe and filtered into a 10 mL sample bottle through organic phase needle filter, and then purified by preparative liquid chromatography. The preparative liquid chromatography was: mobile phase A: $H_2O$, 0.1% HCOOH, mobile phase B: MeCN, 0.1% HCOOH, flow rate 40 mL/min, gradient: 25% B-70% B, 30 minutes, and a peak appeared at 25.1 minutes. The first injection was 5 mL, resulting 45 mL of the preparation solution. 5 mL of acetonitrile was added to the sample bottle again. The second injection was 5 mL, resulting 45 mL of the preparation solution. The obtained preparation solutions were combined into a 250 mL round-bottomed flask, and cooled in a refrigerator at −80° C. for 3 h, and then freeze-dried in a lyophilizer to obtain 102.7 mg of pure Mc-MMAF product. Yield: 52%. LC-MS: (M+H)+: 924.4; (M−H)−: 922.9.

Mc-MMAF Preparation Method 2 (Adding Trifluoroacetic Acid)

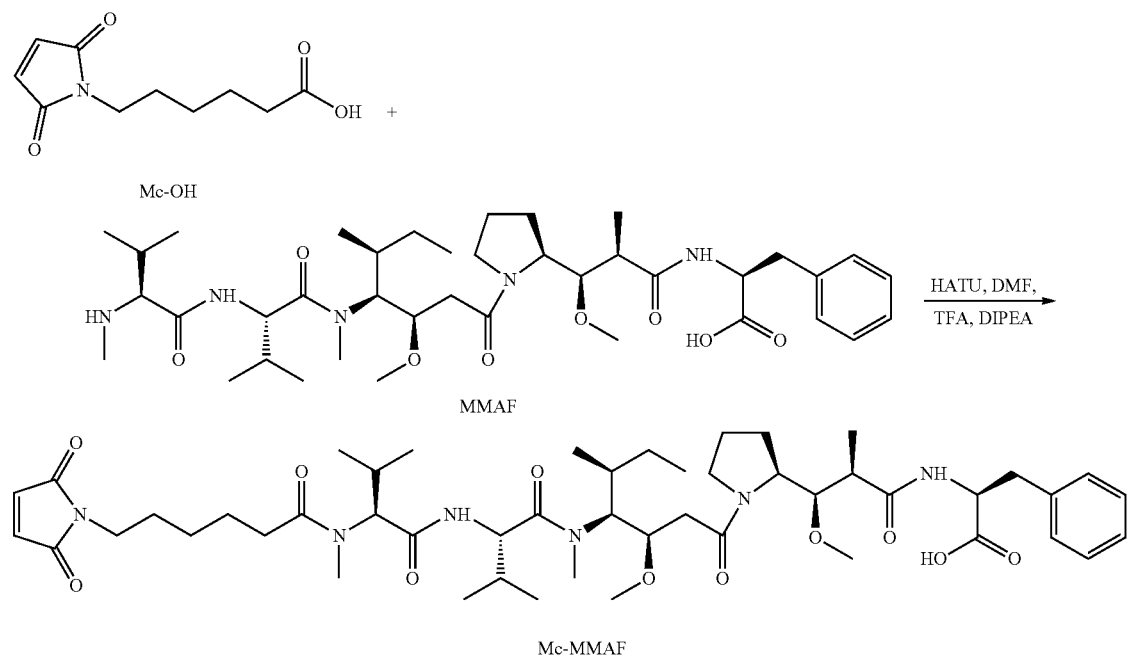

Mc-OH

MMAF

Mc-MMAF 84.8 mg of Mc-OH and 144.7 mg of HATU were weighed and added into a 50 mL round bottom flask, then 5 mL of N,N-dimethylformamide was added into the round bottom flask using a 5 mL syringe, and then 165.4 μL of N,N-diisopropylethylamine was added into the flask using a 200 μL pipettor. The flask was placed on a magnetic stirrer, and after adding a stir bar, stirring was performed at room temperature for 0.5 h. 146.4 mg of MMAF and 22.8 mg of trifluoroacetic acid were weighed and added into a 25 mL round bottom flask, and then 10 mL of N,N-dimethylformamide was added into the flask using a 10 mL syringe. After adding a stir bar, the flask was placed on a magnetic stirrer and stirring was performed in an ice bath. Under the ice bath condition, the Mc-OH system was transferred into the MMAF solution using a 5 mL plastic dropper. The ice bath was removed from the magnetic stirrer, and the mixture was stirred for 1 h. Then, the reaction was stopped, 10 μL of sample was taken and added into a 1.5 mL centrifuge tube using a 10 μL pipettor, and then 1 mL of acetonitrile was added into the centrifuge tube using a 1 mL pipettor. The sample was taken using a 1 ml syringe and passed through organic phase needle filter, and then loaded for LC-MS to check the reaction.

After the reaction was completed, the solvent was spin-dried with a rotary evaporator, and 5 mL of acetonitrile was added. The sample was taken using a 5 mL syringe and filtered into a 10 mL sample bottle through organic phase needle filter, and then purified by preparative liquid chromatography. The preparative liquid chromatography was: mobile phase A: $H_2O$, 0.1% HCOOH, mobile phase B: MeCN, 0.1% HCOOH, flow rate 40 mL/min, gradient: 25% B-70% B, 30 minutes, and a peak appeared at 25.1 minutes. The first injection was 5 mL, resulting 45 mL of the preparation solution. 5 mL of acetonitrile was added to the sample bottle again, and the second injection was 5 mL, resulting 45 mL of the preparation solution. The obtained preparation solutions were combined into a 250 mL round-bottomed flask, and cooled in a refrigerator at −80° C. for 3 h, and then freeze-dried in a lyophilizer to obtain 114.1 mg of pure Mc-MMAF product. Yield: 62%. LC-MS: (M+H)+: 924.4; (M−H)−: 922.9.

Mc-MMAF Preparation Method 3 (Adding p-Toluenesulfonic Acid Monohydrate)

84.6 mg of Mc-OH and 144.2 mg of HATU were weighed and added into a 50 mL round bottom flask, then 5 mL of N,N-dimethylformamide was added into the round bottom flask using a 5 mL syringe, and then 165.4 μL of N,N-diisopropylethylamine was added into the flask using a 200 μL pipettor. The flask was placed on a magnetic stirrer, and after adding a stir bar, stirring was performed at room temperature for 0.5 h. 146.4 mg of MMAF and 34.8 mg of p-toluenesulfonic acid monohydrate were weighed and added into a 25 mL round bottom flask, and then 10 mL of N,N-dimethylformamide was added into the flask using a 10 mL syringe. After adding a stir bar, the flask was placed on a magnetic stirrer and stirring was performed in an ice bath. Under the ice bath condition, the Mc-OH system was transferred into the MMAF solution using a 5 mL plastic dropper. The ice bath was removed from the magnetic stirrer, and the mixture was stirred for another 1 h. Then, the reaction was stopped, 10 μL of sample was taken and added into a 1.5 mL centrifuge tube using a 10 μL pipettor, and then 1 mL of acetonitrile was added into the centrifuge tube using a 1 mL pipettor. The sample was taken using a 1 ml syringe and passed through organic phase needle filter, and then loaded for LC-MS to check the reaction.

After the reaction was completed, the solvent was spin-dried with a rotary evaporator, and 5 mL of acetonitrile was added. The sample was taken using a 5 mL syringe and filtered into a 10 mL sample bottle through organic phase needle filter, and then purified by preparative liquid chromatography. The preparative liquid chromatography was: mobile phase A: $H_2O$, 0.1% HCOOH, mobile phase B: MeCN, 0.1% HCOOH, flow rate 40 mL/min, gradient: 25% B-70% B, 30 minutes, and a peak appeared at 25.1 minutes. The first injection was 5 mL, resulting 45 mL of the preparation solution. 5 mL of acetonitrile was added to the sample bottle again, and the second injection was 5 mL, resulting 45 mL of the preparation solution. The obtained preparation solutions were combined into a 250 mL round-bottomed flask, and cooled in a refrigerator at −80° C. for 3 h, and then freeze-dried in a lyophilizer to obtain 125.9 mg of pure Mc-MMAF product. Yield: 68%. LC-MS: (M+H)+: 924.4; (M−H)−: 922.9.

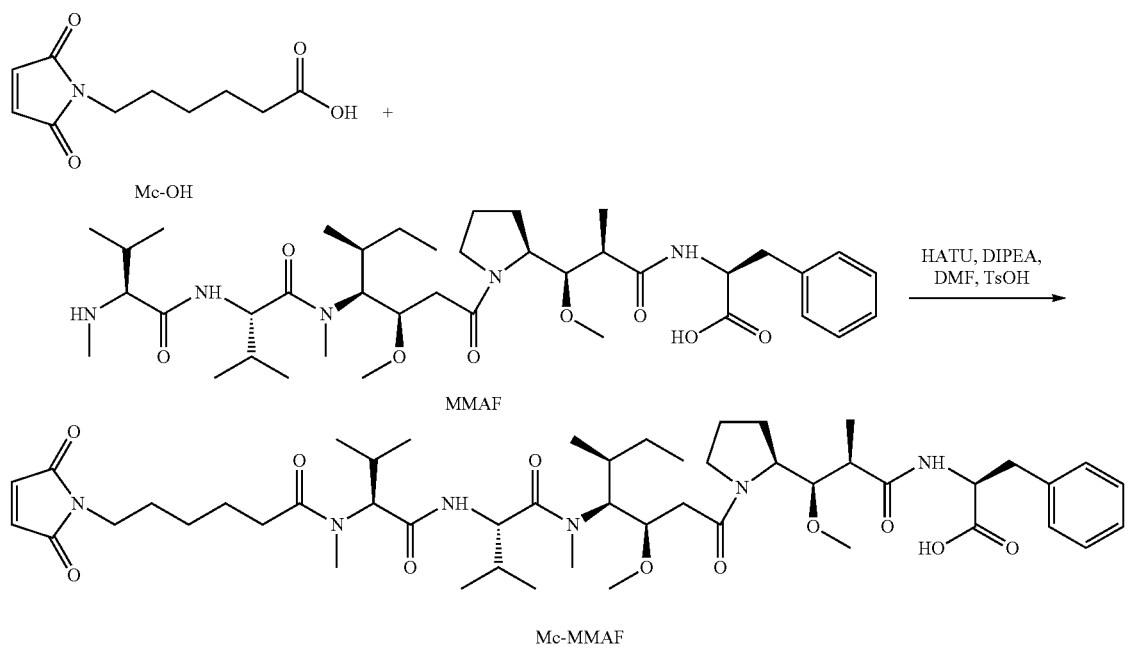

Mc-MMAF Preparation Method 4 (Adding (−)-10-Camphorsulfonic Acid)

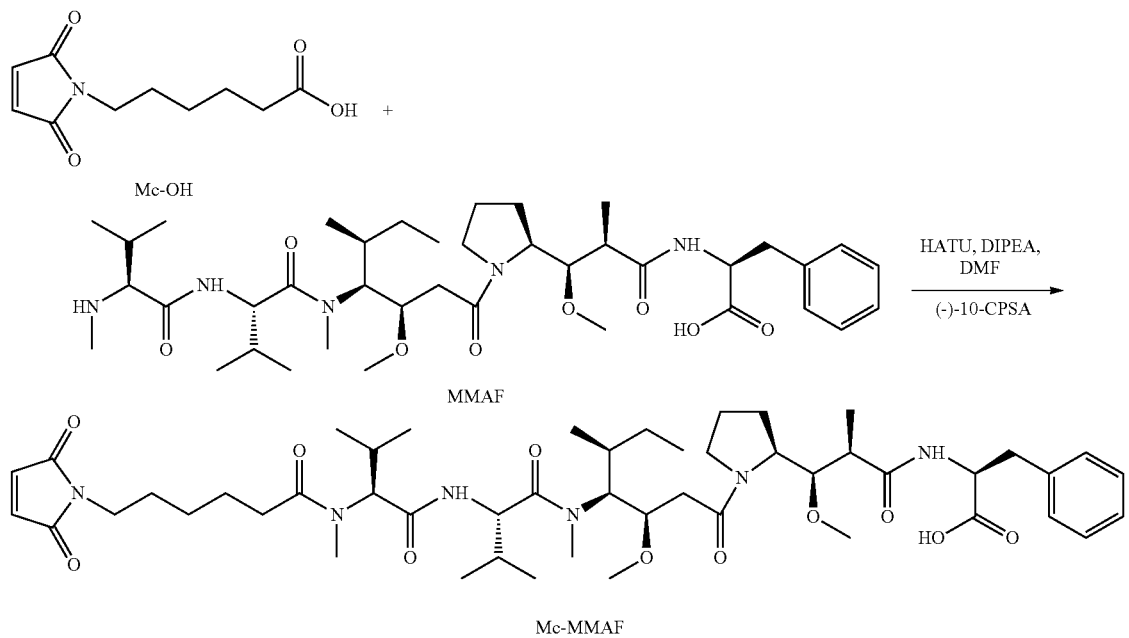

84.2 mg of Mc-OH and 144.4 mg of HATU were weighed and added into a 50 mL round bottom flask, then 5 mL of N,N-dimethylformamide was added into the round bottom flask using a 5 mL syringe, and then 165.4 μL of N,N-diisopropylethylamine was added into the flask using a 200 μL pipettor. The flask was placed on a magnetic stirrer, and after adding a stir bar, stirred at room temperature for 0.5 h. 147.0 mg of MMAF and 46.8 mg of (−)-10-camphorsulfonic acid were weighed and added into a 25 mL round bottom flask, and then 10 mL of N,N-dimethylformamide was added into the flask using a 10 mL syringe. After adding a stir bar, the flask was placed on a magnetic stirrer and stirred in an ice bath. Under the ice bath condition, the Mc-OH system was transferred into the MMAF solution using a 5 mL plastic dropped. The ice bath was removed from the magnetic stirrer, and the mixture was stirred for 1 h. Then, the reaction was stopped, 10 μL of sample was taken and added into a 1.5 mL centrifuge tube using a 10 μL pipettor, and then 1 mL of acetonitrile was added into the centrifuge tube using a 1 mL pipettor. The sample was taken using a 1 ml syringe and passed through organic phase needle filter, and then loaded for LC-MS to check the reaction.

After the reaction was completed, the solvent was spin-dried with a rotary evaporator, and 5 mL of acetonitrile was added. The sample was taken using a 5 mL syringe and filtered into a 10 mL sample bottle through organic phase needle filter, and then purified by preparative liquid chromatography. The preparative liquid chromatography was: mobile phase A: $H_2O$, 0.1% HCOOH, mobile phase B: MeCN, 0.1% HCOOH, flow rate 40 mL/min, gradient: 25% B-70% B, 30 minutes, and a peak appeared at 25.1 minutes. The first injection was 5 mL, resulting 45 mL of the preparation solution. 5 mL of acetonitrile was added to the sample bottle, and the second injection was 5 mL, resulting 45 mL of the preparation solution. The obtained preparation solutions were combined into a 250 mL round-bottomed flask, and cooled in a refrigerator at −80° C. for 3 h, and then freeze-dried in a lyophilizer to obtain 117.4 mg of pure Mc-MMAF product. Yield: 64%. LC-MS: (M+H)+: 924.4; (M−H)−: 922.9.

Mc-MMAF Preparation Method 5 (Adding Trifluoromethanesulfonic Acid)

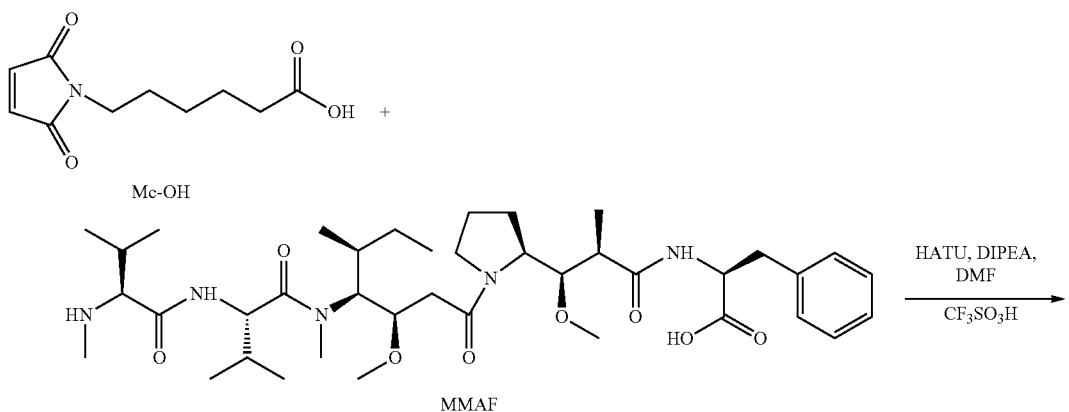

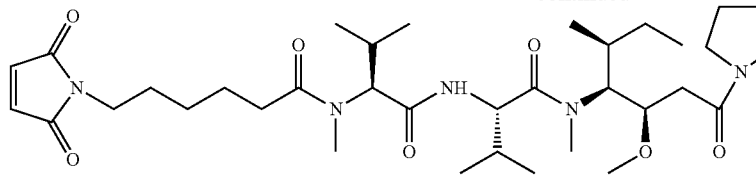 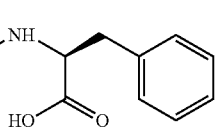

Mc-MMAF 84.6 mg of Mc-OH and 144.7 mg of HATU were weighed and added into a 50 mL round bottom flask, then 5 mL of N,N-dimethylformamide was added into the round bottom flask using a 5 mL syringe, and then 165.4 μL of N,N-diisopropylethylamine was added into the flask using a 200 μL pipettor. The flask was placed on a magnetic stirrer, and after adding a stir bar, stirring was performed at room temperature for 0.5 h. 146.5 mg of MMAF and 30.0 mg of trifluoromethanesulfonic acid were weighed and added into a 25 mL round bottom flask, and then 10 mL of N,N-dimethylformamide was added into the flask using a 10 mL syringe. After adding a stir bar, the flask was placed on a magnetic stirrer and stirring was performed in an ice bath. Under the ice bath condition, the Mc-OH system was transferred into the MMAF solution using a 5 mL plastic dropped. The ice bath was removed from the magnetic stirrer, and the mixture was stirred for 1 h. Then, the reaction was stopped, 10 μL of sample was taken and added into a 1.5 mL centrifuge tube using a 10 μL pipettor, and then 1 mL of acetonitrile was added into the centrifuge tube using a 1 mL pipettor. The sample was taken using a 1 ml syringe and passed through organic phase needle filter, and then loaded for LC-MS to check the reaction.

After the reaction was completed, the solvent was spin-dried with a rotary evaporator, and 5 mL of acetonitrile was added. The sample was taken using a 5 mL syringe and filtered into a 10 mL sample bottle through organic phase needle filter, and then purified by preparative liquid chromatography. The preparative liquid chromatography was: mobile phase A: $H_2O$, 0.1% HCOOH, mobile phase B: MeCN, 0.1% HCOOH, flow rate 40 mL/min, gradient: 25% B-70% B, 30 minutes, and a peak appeared at 25.1 minutes. The first injection was 5 mL, resulting 45 mL of the preparation solution. 5 mL of acetonitrile was added to the sample bottle, and the second injection was 5 mL, resulting 45 mL of the preparation solution. The obtained preparation solutions were combined into a 250 mL round-bottomed flask, and cooled in a refrigerator at −80° C. for 3 h, and then freeze-dried in a lyophilizer to obtain 121.2 mg of pure Mc-MMAF product. Yield: 66%. LC-MS: (M+H)+: 924.4; (M−H)−: 922.9.

In the preliminary test, we made further exploration on the basis of Mc-MMAF preparation method 1 mentioned above. When preparing the MMAF reaction solution, the MMAF was first converted to salts by adding an acid or base reagent and then participated in the reaction. We performed the preliminary test by adding trifluoroacetic acid, potassium tert-butoxide and the like, and found that when formulating MMAF reaction solution by adding potassium tert-butoxide (Mc-MMAF preparation method 2), the yield of Mc-MMAF product was significantly increased.

We then explored the effect of adding other acids, and found that the addition of various acids has a surprising effect on yield. For example, compared with the control, when adding p-toluenesulfonic acid monohydrate (Mc-MMAF preparation method 3), the yield of Mc-MMAF has also been surprisingly improved, from 52% to 68%, that is, the absolute value of the yield has been increased by 16%, and the relative value of the yield has been increased by 30.7% ((68%-52%)/52%) compared with the preparation method 1 without adding acid. In addition, the yields of Mc-MMAF product in the experimental group of adding (−)-10-camphorsulfonic acid and trifluoromethanesulfonic acid also reach 64% and 66%, respectively.

The test results show that by adding an acid reagent to the reaction system, the yield of Mc-MMAF can be effectively improved.

Example 2 Test Results of Adding Various Sulfonic Acids

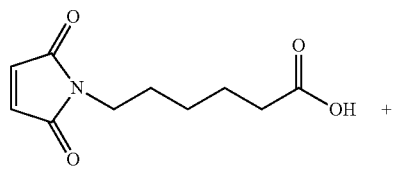

Me-OH +

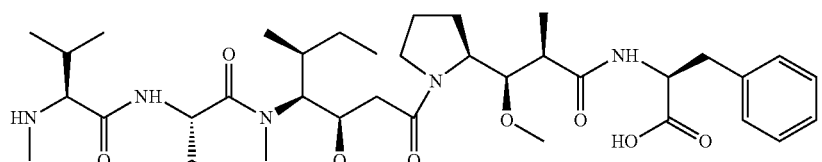

MMAF

1) HATU, DIPEA, DMF, (−)-10-CPSA
2) HATU, DIPEA, DMF, (+)-10-CPSA
3) HATU, DIPEA, DMF, 10-CPSA
4) HATU, DIPEA, DMF, $MeSO_3H$
5) HATU, DIPEA, DMF, $CF_3SO_3H$
6) HATU, DIPEA, DMF, TsOH

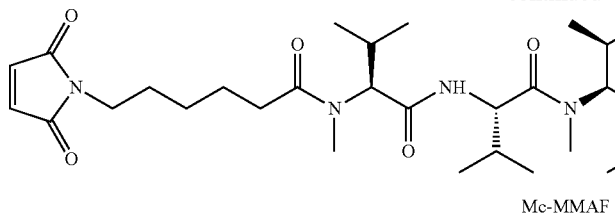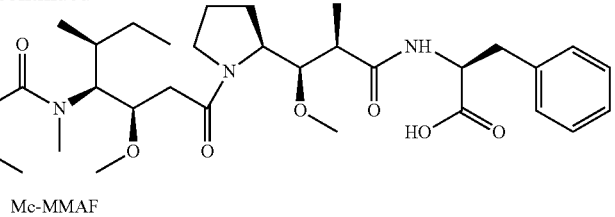

Mc-MMAF

Test 1) Adding (−)-10-Camphorsulfonic Acid 11.5 mg of Mc-OH and 20.5 mg of HATU were weighed and added into a 5 mL flask, then 1 mL of N,N-dimethylformamide was added into the flask using a 1 mL pipettor, and then 22.3 μL of N,N-diisopropylethylamine was added into the flask using a 100 μL pipettor. The flask was placed on a parallel reactor stirrer, and after adding a stir bar, stirring was performed at room temperature for 0.5 h. 20.0 mg of MMAF and 6.3 mg of (−)-10-camphorsulfonic acid were weighed and added into another 5 mL flask, and then 1 mL of N,N-dimethylformamide was added into the flask two times using a 1 mL syringe. After adding a stir bar, the flask was placed on a magnetic stirrer and stirring was performed in an ice bath. Under the ice bath condition, the Mc-OH system was transferred into the MMAF solution using a 5 mL plastic dropper. The reaction flask was placed on the parallel stirrer and the mixture was stirred for 1 h. Then, the reaction was stopped, 10 μL of sample was taken and added into a 1.5 mL centrifuge tube using a 10 μL pipettor, and then 1 mL of acetonitrile was added into the centrifuge tube using a 1 mL pipettor. The sample was taken using a 1 ml syringe and passed through organic phase needle filter, and then loaded for LC-MS to check the reaction.

Test 2) Adding (+)-10-Camphorsulfonic Acid 11.5 mg of Mc-OH and 20.5 mg of HATU were weighed and added into a 5 mL flask, then 1 mL of N,N-dimethylformamide was added into the flask using a 1 mL pipettor, and then 22.3 μL of N,N-diisopropylethylamine was added into the flask using a 100 μL pipettor. The flask was placed on a parallel reactor stirrer, and after adding a stir bar, stirring was performed at room temperature for 0.5 h. 20.0 mg of MMAF and 6.3 mg of (+)-10-camphorsulfonic acid were weighed and added into another 5 mL flask, and then 1 mL of N,N-dimethylformamide was added into the flask two times using a 1 mL syringe. After adding a stir bar, the flask was placed on a magnetic stirrer and stirring was performed in an ice bath. Under the ice bath condition, the Mc-OH system was transferred into the MMAF solution using a 5 mL plastic dropper. The reaction flask was placed on the parallel stirrer and the mixture was stirred for 1 h. Then, the reaction was stopped, 10 μL of sample was taken and added into a 1.5 mL centrifuge tube using a 10 μL pipettor, and then 1 mL of acetonitrile was added into the centrifuge tube using a 1 mL pipettor. The sample was taken using a 1 ml syringe and passed through organic phase needle filter, and then loaded for LC-MS to check the reaction.

Test 3) Adding 10-Camphorsulfonic Acid 11.5 mg of Mc-OH and 20.5 mg of HATU were weighed and added into a 5 mL flask, then 1 mL of N,N-dimethylformamide was added into the flask using a 1 mL pipettor, and then 22.3 μL of N,N-diisopropylethylamine was added into the flask using a 100 μL pipettor. The flask was placed on a parallel reactor stirrer, and after adding a stir bar, stirring was performed at room temperature for 0.5 h. 20.0 mg of MMAF and 6.3 mg of 10-camphorsulfonic acid were weighed and added into another 5 mL flask, and then 1 mL of N,N-dimethylformamide was added into the flask two times using a 1 mL syringe. After adding a stir bar, the flask was placed on a magnetic stirrer and stirring was performed in an ice bath. Under the ice bath condition, the Mc-OH system was transferred into the MMAF solution using a 5 mL plastic dropper. The reaction flask was placed on the parallel stirrer and the mixture was stirred for 1 h. Then, the reaction was stopped, 10 μL of sample was taken and added into a 1.5 mL centrifuge tube using a 10 μL pipettor, and then 1 mL of acetonitrile was added into the centrifuge tube using a 1 mL pipettor. The sample was taken using a 1 ml syringe and passed through organic phase needle filter, and then loaded for LC-MS to check the reaction.

Test 4) Adding Methanesulfonic Acid 11.5 mg of Mc-OH and 20.5 mg of HATU were weighed and added into a 5 mL flask, then 1 mL of N,N-dimethylformamide was added into the flask using a 1 mL pipettor, and then 22.3 μL of N,N-diisopropylethylamine was added into the flask using a 100 μL pipettor. The flask was placed on a parallel reactor stirrer, and after adding a stir bar, stirring was performed at room temperature for 0.5 h. 20.0 mg of MMAF and 2.6 mg of methanesulfonic acid were weighed and added into another 5 mL flask, and then 1 mL of N,N-dimethylformamide was added into the flask two times using a 1 mL syringe. After adding a stir bar, the flask was placed on a magnetic stirrer and stirring was performed in an ice bath. Under the ice bath condition, the Mc-OH system was transferred into the MMAF solution using a 5 mL plastic dropper. The reaction flask was placed on the parallel stirrer and the mixture was stirred for 1 h. Then, the reaction was stopped, 10 μL of sample was taken and added into a 1.5 mL centrifuge tube using a 10 μL pipettor, and then 1 mL of acetonitrile was added into the centrifuge tube using a 1 mL pipettor. The sample was taken using a 1 ml syringe and passed through organic phase needle filter, and then loaded for LC-MS to check the reaction.

Test 5) Adding Trifluoromethanesulfonic Acid 11.5 mg of Mc-OH and 20.5 mg of HATU were weighed and added into a 5 mL flask, then 1 mL of N,N-dimethylformamide was added into the flask using a 1 mL pipettor, and then 22.3 μL of N,N-diisopropylethylamine was added into the flask using a 100 μL pipettor. The flask was placed on a parallel reactor stirrer, and after adding a stir bar, stirring was performed at room temperature for 0.5 h. 20.0 mg of MMAF and 4.1 mg of trifluoromethanesulfonic acid were weighed and added into another 5 mL flask, and then 1 mL of N,N-dimethylformamide was added into the flask two times using a 1 mL syringe. After adding a stir bar, the flask was placed on a magnetic stirrer and stirring was performed in an ice bath. Under the ice bath condition, the Mc-OH system was transferred into the MMAF solution using a 5 mL plastic dropper. The reaction flask was placed on the parallel stirrer and the mixture was stirred for 1 h. Then, the reaction was stopped, 10 μL of sample was taken and added into a 1.5 mL centrifuge tube using a 10 μL pipettor, and then 1 mL of acetonitrile was added into the centrifuge tube using a 1 mL pipettor. The sample was taken using a 1 ml syringe and passed through organic phase needle filter, and then loaded for LC-MS to check the reaction.

Test 6) Adding p-Toluenesulfonic Acid Monohydrate 11.5 mg of Mc-OH and 20.5 mg of HATU were weighed and added into a 5 mL flask, then 1 mL of N,N-dimethylformamide was added into the flask using a 1 mL pipettor, and then 22.3 μL of N,N-diisopropylethylamine was added into the flask using a 100 μL pipettor. The flask was placed on a parallel reactor stirrer, and after adding a stir bar, stirring was performed at room temperature for 0.5 h. 20.0 mg of MMAF and 4.7 mg of p-toluenesulfonic acid monohydrate were weighed and added into another 5 mL flask, and then 1 mL of N,N-dimethylformamide was added into the flask two times using a 1 mL syringe. After adding a stir bar, the flask was placed on a magnetic stirrer and stirring was performed in an ice bath. Under the ice bath condition, the Mc-OH system was transferred into the MMAF solution using a 5 mL plastic dropper. The reaction flask was placed on the parallel stirrer and the mixture was stirred for 1 h. Then, the reaction was stopped, 10 μL of sample was taken and added into a 1.5 mL centrifuge tube using a 10 μL pipettor, and then 1 mL of acetonitrile was added into the centrifuge tube using a 1 mL pipettor. The sample was taken using a 1 ml syringe and passed through organic phase needle filter, and then loaded for LC-MS to check the reaction.

The test results are shown in FIG. 1. The addition of various types of sulfonic acids, such as (−)-10-camphorsulfonic acid, (+)-10-camphorsulfonic acid, 10-camphorsulfonic acid, methanesulfonic acid, and trifluoromethanesulfonic acid in the reaction system can achieve a reaction promoting effect equivalent to the addition of p-toluenesulfonic acid monohydrate, and can effectively improve the yield of Mc-MMAF.

Example 3 Effect of Different Amounts of the Acid Additive

Test 1) without Acid Additive 11.5 mg (0.055 mmol) of Mc-OH and 20.5 (0.054 mmol) mg of HATU were weighed and added into a 5 mL flask, then 1 mL of N,N-dimethylformamide was added into the flask using a 1 mL pipettor, and then 35.7 μL (0.216 mmol) of N,N-diisopropylethylamine was added into the flask using a 100 μL pipettor. The flask was placed on a parallel reactor stirrer, and after adding a stir bar, stirring was performed at room temperature for 0.5 h. 20.0 mg (0.027 mmol) of MMAF was weighed and added into another 5 mL flask, and then 1 mL of N,N-dimethylformamide was added into the flask two times using a 1 mL syringe. After adding a stir bar, the flask was placed on a magnetic stirrer and stirring was performed in an ice bath. Under the ice bath condition, the Mc-OH system was transferred into the MMAF solution using a 5 mL plastic dropper. The reaction flask was placed on the parallel stirrer and the mixture was stirred for 1 h. Then, the reaction was stopped, 10 μL of sample was taken and added into a 1.5 mL centrifuge tube using a 10 μL pipettor, and then 1 mL of acetonitrile was added into the centrifuge tube using a 1 mL pipettor. The sample was taken using a 1 ml syringe and passed through organic phase needle filter, and then loaded for LC-MS to check the reaction.

Test 2) the Molar Ratio of the Acid to MMAF at 1:100

11.5 mg of Mc-OH and 20.5 mg of HATU were weighed and added into a 5 mL flask, then 1 mL of N,N-dimethylformamide was added into the flask using a 1 mL pipettor, and then 35.7 μL of N,N-diisopropylethylamine was added into the flask using a 100 μL pipettor. The flask was placed on a parallel reactor stirrer, and after adding a stir bar, stirring was performed at room temperature for 0.5 h. 20.0 mg of MMAF and 46 μg ($2.7*10^{-4}$ mmol) of p-toluenesulfonic acid monohydrate were weighed and added into another 5 mL flask, and then 1 mL of N,N-dimethylformamide was added into the flask two times using a 1 mL syringe. After adding a stir bar, the flask was placed on a magnetic stirrer and stirring was performed in an ice bath. Under the ice bath condition, the Mc-OH system was transferred into the MMAF solution using a 5 mL plastic dropper. The reaction flask was placed on the parallel stirrer and the mixture was stirred for 1 h. Then, the reaction was stopped, 10 μL of sample was taken and added into a 1.5 mL centrifuge tube using a 10 μL pipettor, and then 1 mL of acetonitrile was added into the centrifuge tube using a 1 mL pipettor. The sample was taken using a 1 ml syringe and passed through organic phase needle filter, and then loaded for LC-MS to check the reaction.

Test 3) the Molar Ratio of the Acid Additive to MMAF at 1:20

11.5 mg of Mc-OH and 20.5 mg of HATU were weighed and added into a 5 mL flask, then 1 mL of N,N-dimethylformamide was added into the flask using a 1 mL pipettor, and then 35.7 μL of N,N-diisopropylethylamine was added into the flask using a 100 μL pipettor. The flask was placed on a parallel reactor stirrer, and after adding a stir bar, stirring was performed at room temperature for 0.5 h. 20.0 mg of MMAF and 0.23 mg ($13.5*10^{-4}$ mmol) of p-toluenesulfonic acid monohydrate were weighed and added into another 5 mL flask, and then 1 mL of N,N-dimethylformamide was added into the flask two times using a 1 mL syringe. After adding a stir bar, the flask was placed on a magnetic stirrer and stirring was performed in an ice bath. Under the ice bath condition, the Mc-OH system was transferred into the MMAF solution using a 5 mL plastic dropper. The reaction flask was placed on the parallel stirrer and the mixture was stirred for 1 h. Then, the reaction was stopped, 10 μL of sample was taken and added into a 1.5 mL centrifuge tube using a 10 μL pipettor, and then 1 mL of acetonitrile was added into the centrifuge tube using a 1 mL pipettor. The sample was taken using a 1 ml syringe and passed through organic phase needle filter, and then loaded for LC-MS to check the reaction.

Test 4) the Molar Ratio of the Acid Additive to MMAF at 1:10

11.5 mg of Mc-OH and 20.5 mg of HATU were weighed and added into a 5 mL flask, then 1 mL of N,N-dimethylformamide was added into the flask using a 1 mL pipettor, and then 35.7 μL of N,N-diisopropylethylamine was added into the flask using a 100 μL pipettor. The flask was placed on a parallel reactor stirrer, and after adding a stir bar, stirring was performed at room temperature for 0.5 h. 20.0 mg of MMAF and 0.46 mg ($2.7*10^{-3}$ mmol) of p-toluenesulfonic acid monohydrate were weighed and added into another 5 mL flask, and then 1 mL of N,N-dimethylformamide was added into the flask two times using a 1 mL syringe. After adding a stir bar, the flask was placed on a magnetic stirrer and stirring was performed in an ice bath.

Under the ice bath condition, the Mc-OH system was transferred into the MMAF solution using a 5 mL plastic dropper. The reaction flask was placed on the parallel stirrer and the mixture was stirred for 1 h. Then, the reaction was stopped, 10 μL of sample was taken and added into a 1.5 mL centrifuge tube using a 10 μL pipettor, and then 1 mL of acetonitrile was added into the centrifuge tube using a 1 mL pipettor. The sample was taken using a 1 ml syringe and passed through organic phase needle filter, and then loaded for LC-MS to check the reaction.

Test 5) the Molar Ratio of the Acid Additive to MMAF at 1:5

11.5 mg of Mc-OH and 20.5 mg of HATU were weighed and added into a 5 mL flask, then 1 mL of N,N-dimethylformamide was added into the flask using a 1 mL pipettor, and then 35.7 μL of N,N-diisopropylethylamine was added into the flask using a 100 μL pipettor. The flask was placed on a parallel reactor stirrer, and after adding a stir bar, stirring was performed at room temperature for 0.5 h. 20.0 mg of MMAF and 0.92 mg ($5.4*10^{-3}$ mmol) of p-toluenesulfonic acid monohydrate were weighed and added into another 5 mL flask, and then 1 mL of N,N-dimethylformamide was added into the flask two times using a 1 mL syringe. After adding a stir bar, the flask was placed on a magnetic stirrer and stirring was performed in an ice bath. Under the ice bath condition, the Mc-OH system was transferred into the MMAF solution using a 5 mL plastic dropper. The reaction flask was placed on the parallel stirrer and the mixture was stirred for 1 h. Then, the reaction was stopped, 10 μL of sample was taken and added into a 1.5 mL centrifuge tube using a 10 μL pipettor, and then 1 mL of acetonitrile was added into the centrifuge tube using a 1 mL pipettor. The sample was taken using a 1 ml syringe and passed through organic phase needle filter, and then loaded for LC-MS to check the reaction.

Test 6) the Molar Ratio of the Acid Additive to MMAF at 2:5

11.5 mg of Mc-OH and 20.5 mg of HATU were weighed and added into a 5 mL flask, then 1 mL of N,N-dimethylformamide was added into the flask using a 1 mL pipettor, and then 35.7 μL of N,N-diisopropylethylamine was added into the flask using a 100 μL pipettor. The flask was placed on a parallel reactor stirrer, and after adding a stir bar, stirring was performed at room temperature for 0.5 h. 20.0 mg of MMAF and 1.84 mg (0.011 mmol) of p-toluenesulfonic acid monohydrate were weighed and added into another 5 mL flask, and then 1 mL of N,N-dimethylformamide was added into the flask two times using a 1 mL syringe. After adding a stir bar, the flask was placed on a magnetic stirrer and stirring was performed in an ice bath. Under the ice bath condition, the Mc-OH system was transferred into the MMAF solution using a 5 mL plastic dropper. The reaction flask was placed on the parallel stirrer and the mixture was stirred for 1 h. Then, the reaction was stopped, 10 μL of sample was taken and added into a 1.5 mL centrifuge tube using a 10 μL pipettor, and then 1 mL of acetonitrile was added into the centrifuge tube using a 1 mL pipettor. The sample was taken using a 1 ml syringe and passed through organic phase needle filter, and then loaded for LC-MS to check the reaction.

Test 7) the Molar Ratio of the Acid Additive to MMAF at 1:2

11.5 mg of Mc-OH and 20.5 mg of HATU were weighed and added into a 5 mL flask, then 1 mL of N,N-dimethylformamide was added into the flask using a 1 mL pipettor, and then 35.7 μL of N,N-diisopropylethylamine was added into the flask using a 100 μL pipettor. The flask was placed on a parallel reactor stirrer, and after adding a stir bar, stirring was performed at room temperature for 0.5 h. 20.0 mg of MMAF and 2.3 mg (0.014 mmol) of p-toluenesulfonic acid monohydrate were weighed and added into another 5 mL flask, and then 1 mL of N,N-dimethylformamide was added into the flask two times using a 1 mL syringe. After adding a stir bar, the flask was placed on a magnetic stirrer and stirring was performed in an ice bath. Under the ice bath condition, the Mc-OH system was transferred into the MMAF solution using a 5 mL plastic dropper. The reaction flask was placed on the parallel stirrer and the mixture was stirred for 1 h. Then, the reaction was stopped, 10 μL of sample was taken and added into a 1.5 mL centrifuge tube using a 10 μL pipettor, and then 1 mL of acetonitrile was added into the centrifuge tube using a 1 mL pipettor. The sample was taken using a 1 ml syringe and passed through organic phase needle filter, and then loaded for LC-MS to check the reaction.

Test 8) the Molar Ratio of the Acid Additive to MMAF at 1:1

11.5 mg of Mc-OH and 20.5 mg of HATU were weighed and added into a 5 mL flask, then 1 mL of N,N-dimethylformamide was added into the flask using a 1 mL pipettor, and then 35.7 μL of N,N-diisopropylethylamine was added into the flask using a 100 μL pipettor. The flask was placed on a parallel reactor stirrer, and after adding a stir bar, stirring was performed at room temperature for 0.5 h. 20.0 mg of MMAF and 4.6 mg (0.027 mmol) of p-toluenesulfonic acid monohydrate were weighed and added into another 5 mL flask, and then 1 mL of N,N-dimethylformamide was added into the flask two times using a 1 mL syringe. After adding a stir bar, the flask was placed on a magnetic stirrer and stirring was performed in an ice bath. Under the ice bath condition, the Mc-OH system was transferred into the MMAF solution using a 5 mL plastic dropper. The reaction flask was placed on the parallel stirrer and the mixture was stirred for 1 h. Then, the reaction was stopped, 10 μL of sample was taken and added into a 1.5 mL centrifuge tube using a 10 μL pipettor, and then 1 mL of acetonitrile was added into the centrifuge tube using a 1 mL pipettor. The sample was taken using a 1 ml syringe and passed through organic phase needle filter, and then loaded for LC-MS to check the reaction.

Test 9) the Molar Ratio of the Acid Additive to MMAF at 2:1

11.5 mg of Mc-OH and 20.5 mg of HATU were weighed and added into a 5 mL flask, then 1 mL of N,N-dimethylformamide was added into the flask using a 1 mL pipettor, and then 35.7 μL of N,N-diisopropylethylamine was added into the flask using a 100 μL pipettor. The flask was placed on a parallel reactor stirrer, and after adding a stir bar, stirring was performed at room temperature for 0.5 h. 20.0 mg of MMAF and 9.3 mg (0.054 mmol) of p-toluenesulfonic acid monohydrate were weighed and added into another 5 mL flask, and then 1 mL of N,N-dimethylformamide was added into the flask two times using a 1 mL syringe. After adding a stir bar, the flask was placed on a magnetic stirrer and stirring was performed in an ice bath. Under the ice bath condition, the Mc-OH system was transferred into the MMAF solution using a 5 mL plastic dropper. The reaction flask was placed on the parallel stirrer and the mixture was stirred for 1 h. Then, the reaction was stopped, 10 μL of sample was taken and added into a 1.5 mL centrifuge tube using a 10 μL pipettor, and then 1 mL of acetonitrile was added into the centrifuge tube using a 1 mL pipettor. The sample was taken using a 1 ml syringe and passed through organic phase needle filter, and then loaded for LC-MS to check the reaction.

Test 10) the Molar Ratio of the Acid Additive to MMAF at 3:1

11.5 mg of Mc-OH and 20.5 mg of HATU were weighed and added into a 5 mL flask, then 1 mL of N,N-dimethylformamide was added into the flask using a 1 mL pipettor, and then 35.7 μL of N,N-diisopropylethylamine was added into the flask using a 100 μL pipettor. The flask was placed on a parallel reactor stirrer, and after adding a stir bar, stirring was performed at room temperature for 0.5 h. 20.0 mg of MMAF and 13.9 mg (0.081 mmol) of p-toluenesulfonic acid monohydrate were weighed and added into another 5 mL flask, and then 1 mL of N,N-dimethylformamide was added into the flask two times using a 1 mL syringe. After adding a stir bar, the flask was placed on a magnetic stirrer and stirring was performed in an ice bath. Under the ice bath condition, the Mc-OH system was transferred into the MMAF solution using a 5 mL plastic dropper. The reaction flask was placed on the parallel stirrer and the mixture was stirred for 1 h. Then, the reaction was stopped, 10 μL of sample was taken and added into a 1.5 mL centrifuge tube using a 10 μL pipettor, and then 1 mL of acetonitrile was added into the centrifuge tube using a 1 mL pipettor. The sample was taken using a 1 ml syringe and passed through organic phase needle filter, and then loaded for LC-MS to check the reaction.

Test 11) the Molar Ratio of the Acid Additive to MMAF at 4:1

11.5 mg of Mc-OH and 20.5 mg of HATU were weighed and added into a 5 mL flask, then 1 mL of N,N-dimethylformamide was added into the flask using a 1 mL pipettor, and then 35.7 μL of N,N-diisopropylethylamine was added into the flask using a 100 μL pipettor. The flask was placed on a parallel reactor stirrer, and after adding a stir bar, stirring was performed at room temperature for 0.5 h. 20.0 mg of MMAF and 18.6 mg (0.108 mmol) of p-toluenesulfonic acid monohydrate were weighed and added into another 5 mL flask, and then 1 mL of N,N-dimethylformamide was added into the flask two times using a 1 mL syringe. After adding a stir bar, the flask was placed on a magnetic stirrer and stirring was performed in an ice bath. Under the ice bath condition, the Mc-OH system was transferred into the MMAF solution using a 5 mL plastic dropper. The reaction flask was placed on the parallel stirrer and the mixture was stirred for 1 h. Then, the reaction was stopped, 10 μL of sample was taken and added into a 1.5 mL centrifuge tube using a 10 μL pipettor, and then 1 mL of acetonitrile was added into the centrifuge tube using a 1 mL pipettor. The sample was taken using a 1 ml syringe and passed through organic phase needle filter, and then loaded for LC-MS to check the reaction.

Figure 2:
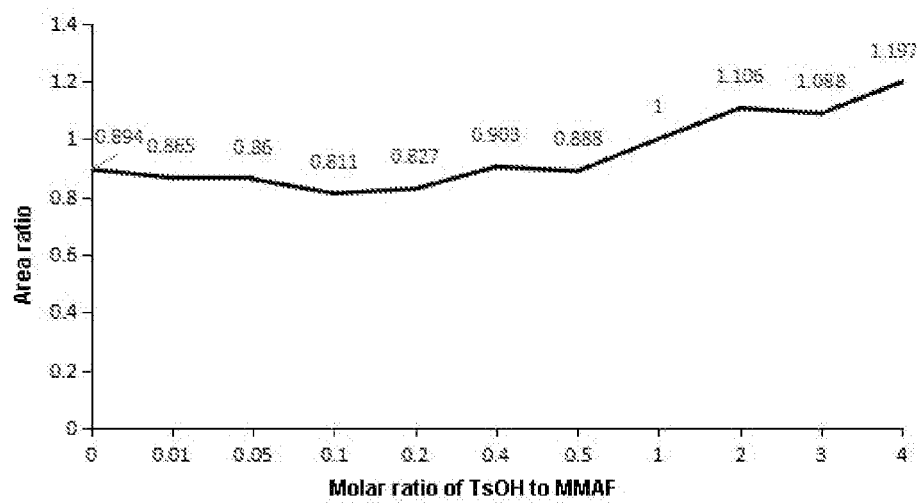
FIG. 2 is a line chart of the area ratio (area ratio refers to the ratio of the peak area of the product in the chromatogram to the reference area, wherein reference area is the peak area when the molar ratio of the acid additive to MMAF is equal to 1:1) of the reaction products obtained by adding different molar amounts of p-toluenesulfonic acid monohydrate in Example 3 of the present invention.

The test results are shown in FIG. 2. When the molar ratio of the acid to MMAF is greater than 1, the reaction is significantly promoted.

Example 4 Effect of Different Amounts of the Organic Base in Solution 1

In order to verify whether the amount of the organic base used in the solution 1 (a solution containing a linking group) affects the result of the reaction, DIPEA was used in the example to further carry out related experiments.

Test 1) Molar Ratio of the Basic Additive (DIPEA) to the Acid Additive at 2:1

11.5 mg (0.055 mmol) of Mc-OH and 20.5 mg (0.054 mmol) mg of HATU were weighed and added into a 5 mL flask, then 1 mL of N,N-dimethylformamide was added into the flask using a 1 mL pipettor, and then 8.9 μL (0.055 mmol) of N,N-diisopropylethylamine was added into the flask using a 100 μL pipettor. The flask was placed on a parallel reactor stirrer, and after adding a stir bar, stirring was performed at room temperature for 0.5 h. 20.0 mg (0.027 mmol) of MMAF and 4.6 mg (0.027 mmol) of p-toluenesulfonic acid monohydrate were weighed and added into another 5 mL flask, and then 1 mL of N,N-dimethylformamide was added into the flask two times using a 1 mL syringe. After adding a stir bar, the flask was placed on a magnetic stirrer and stirring was performed in an ice bath. Under the ice bath condition, the Mc-OH system was transferred into the MMAF solution using a 5 mL plastic dropper. The reaction flask was placed on the parallel stirrer and the mixture was stirred for 1 h. Then, the reaction was stopped, 10 μL of sample was taken and added into a 1.5 mL centrifuge tube using a 10 μL pipettor, and then 1 mL of acetonitrile was added into the centrifuge tube using a 1 mL pipettor. The sample was taken using a 1 ml syringe and passed through organic phase needle filter, and then loaded for LC-MS to check the reaction.

Test 2) Molar Ratio of the Basic Additive (DIPEA) to the Acid Additive at 3:1

11.5 mg of Mc-OH and 20.5 mg of HATU were weighed and added into a 5 mL flask, then 1 mL of N,N-dimethylformamide was added into the flask using a 1 mL pipettor, and then 13.4 μL (0.081 mmol) of N,N-diisopropylethylamine was added into the flask using a 100 μL pipettor. The flask was placed on a parallel reactor stirrer, and after adding a stir bar, stirring was performed at room temperature for 0.5 h. 20.0 mg of MMAF and 4.6 mg of p-toluenesulfonic acid monohydrate were weighed and added into another 5 mL flask, and then 1 mL of N,N-dimethylformamide was added into the flask two times using a 1 mL syringe. After adding a stir bar, the flask was placed on a magnetic stirrer and stirring was performed in an ice bath. Under the ice bath condition, the Mc-OH system was transferred into the MMAF solution using a 5 mL plastic dropper. The reaction flask was placed on the parallel stirrer and the mixture was stirred for 1 h. Then, the reaction was stopped, 10 μL of sample was taken and added into a 1.5 mL centrifuge tube using a 10 μL pipettor, and then 1 mL of acetonitrile was added into the centrifuge tube using a 1 mL pipettor. The sample was taken using a 1 ml syringe and passed through organic phase needle filter, and then loaded for LC-MS to check the reaction.

Test 3) Molar Ratio of the Basic Additive (DIPEA) to the Acid Additive at 4:1

11.5 mg of Mc-OH and 20.5 mg of HATU were weighed and added into a 5 mL flask, then 1 mL of N,N-dimethylformamide was added into the flask using a 1 mL pipettor, and then 17.9 μL (0.108 mmol) of N,N-diisopropylethylamine was added into the flask using a 100 μL pipettor. The flask was placed on a parallel reactor stirrer, and after adding a stir bar, stirring was performed at room temperature for 0.5 h. 20.0 mg of MMAF and 4.6 mg of p-toluenesulfonic acid monohydrate were weighed and added into another 5 mL flask, and then 1 mL of N,N-dimethylformamide was added into the flask two times using a 1 mL syringe. After adding a stir bar, the flask was placed on a magnetic stirrer and stirring was performed in an ice bath. Under the ice bath condition, the Mc-OH system was transferred into the MMAF solution using a 5 mL plastic dropper. The reaction flask was placed on the parallel stirrer and the mixture was stirred for 1 h. Then, the reaction was stopped, 10 μL of sample was taken and added into a 1.5 mL centrifuge tube using a 10 μL pipettor, and then 1 mL of acetonitrile was added into the centrifuge tube using a 1 mL pipettor. The sample was taken using a 1 ml syringe and passed through organic phase needle filter, and then loaded for LC-MS to check the reaction.

Test 4) Molar Ratio of the Basic Additive (DIPEA) to the Acid Additive at 5:1

11.5 mg of Mc-OH and 20.5 mg of HATU were weighed and added into a 5 mL flask, then 1 mL of N,N-dimethylformamide was added into the flask using a 1 mL pipettor, and then 22.3 µL (0.135 mmol) of N,N-diisopropylethylamine was added into the flask using a 100 µL pipettor. The flask was placed on a parallel reactor stirrer, and after adding a stir bar, stirring was performed at room temperature for 0.5 h. 20.0 mg of MMAF and 4.6 mg of p-toluenesulfonic acid monohydrate were weighed and added into another 5 mL flask, and then 1 mL of N,N-dimethylformamide was added into the flask two times using a 1 mL syringe. After adding a stir bar, the flask was placed on a magnetic stirrer and stirring was performed in an ice bath. Under the ice bath condition, the Mc-OH system was transferred into the MMAF solution using a 5 mL plastic dropper. The reaction flask was placed on the parallel stirrer and the mixture was stirred for 1 h. Then, the reaction was stopped, 10 µL of sample was taken and added into a 1.5 mL centrifuge tube using a 10 µL pipettor, and then 1 mL of acetonitrile was added into the centrifuge tube using a 1 mL pipettor. The sample was taken using a 1 ml syringe and passed through organic phase needle filter, and then loaded for LC-MS to check the reaction.

Test 5) Molar Ratio of the Basic Additive (DIPEA) to the Acid Additive at 6:1

11.5 mg of Mc-OH and 20.5 mg of HATU were weighed and added into a 5 mL flask, then 1 mL of N,N-dimethylformamide was added into the flask using a 1 mL pipettor, and then 26.8 µL (0.162 mmol) of N,N-diisopropylethylamine was added into the flask using a 100 µL pipettor. The flask was placed on a parallel reactor stirrer, and after adding a stir bar, stirring was performed at room temperature for 0.5 h. 20.0 mg of MMAF and 4.6 mg of p-toluenesulfonic acid monohydrate were weighed and added into another 5 mL flask, and then 1 mL of N,N-dimethylformamide was added into the flask two times using a 1 mL syringe. After adding a stir bar, the flask was placed on a magnetic stirrer and stirring was performed in an ice bath. Under the ice bath condition, the Mc-OH system was transferred into the MMAF solution using a 5 mL plastic dropper. The reaction flask was placed on the parallel stirrer and the mixture was stirred for 1 h. Then, the reaction was stopped, 10 µL of sample was taken and added into a 1.5 mL centrifuge tube using a 10 µL pipettor, and then 1 mL of acetonitrile was added into the centrifuge tube using a 1 mL pipettor. The sample was taken using a 1 ml syringe and passed through organic phase needle filter, and then loaded for LC-MS to check the reaction.

Test 6) Molar Ratio of the Basic Additive (DIPEA) to the Acid Additive at 7:1

11.5 mg of Mc-OH and 20.5 mg of HATU were weighed and added into a 5 mL flask, then 1 mL of N,N-dimethylformamide was added into the flask using a 1 mL pipettor, and then 31.3 µL (0.189 mmol) of N,N-diisopropylethylamine was added into the flask using a 100 µL pipettor. The flask was placed on a parallel reactor stirrer, and after adding a stir bar, stirring was performed at room temperature for 0.5 h. 20.0 mg of MMAF and 4.6 mg of p-toluenesulfonic acid monohydrate were weighed and added into another 5 mL flask, and then 1 mL of N,N-dimethylformamide was added into the flask two times using a 1 mL syringe. After adding a stir bar, the flask was placed on a magnetic stirrer and stirring was performed in an ice bath. Under the ice bath condition, the Mc-OH system was transferred into the MMAF solution using a 5 mL plastic dropper. The reaction flask was placed on the parallel stirrer and the mixture was stirred for 1 h. Then, the reaction was stopped, 10 µL of sample was taken and added into a 1.5 mL centrifuge tube using a 10 µL pipettor, and then 1 mL of acetonitrile was added into the centrifuge tube using a 1 mL pipettor. The sample was taken using a 1 ml syringe and passed through organic phase needle filter, and then loaded for LC-MS to check the reaction.

Figure 3:
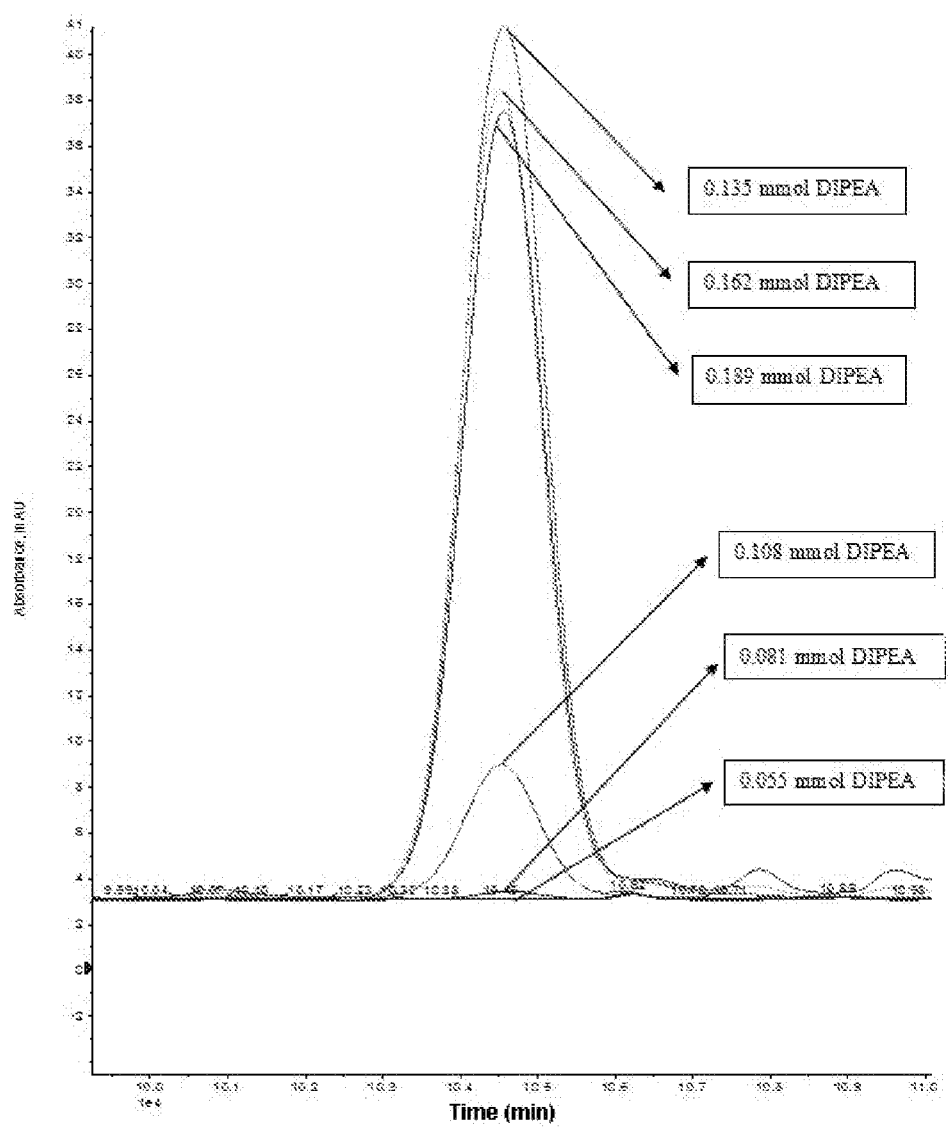
FIG. 3 is a liquid chromatogram of the products obtained by adding different molar amounts of N,N-diisopropylethylamine in Example 4 of the present invention.

In the entire reaction system, when the addition amount of MMAF is 0.027 mmol, the addition amount of Mc-OH is 0.055 mmol, the acid reagent is 0.027 mmol, and the total free carboxyl group present in the reaction system is 0.109 mmol. According to the test result shown in FIG. 3, when the molar amount of DIPEA added is less than or equal to 0.108 mmol, there is no reaction or the reaction rate is low; and when the molar amount of DIPEA is greater than 0.108 mmol, that is, the molar amount of organic base in the system is greater than that of the free carboxyl groups in the reaction system, the reaction is promoted remarkably.

It is easy to see from the above examples that compared to the case where no acid was added (the preparation method 1 in Example 1), the method provided by the present invention (ie, the preparation of antibody-drug conjugate intermediate by addition of acid) significantly improves the yield of Mc-MMAF, which is an unexpected technical effect.

Therefore, according to the above-mentioned principle verified by the synthesis of Mc-MMAF as a test example, it can be inferred that converting the monomethyl auristatin derivative into a salt by adding an acid reagent to participate in the reaction can significantly promote the reaction and greatly improve the yield. In addition, the method not only reduces the cost of the consumables, labor, equipment, site, raw materials and the like in the production, but also greatly reduces the production of the waste liquid, and thus reduces production costs and improves production efficiency, and is suitable for industrial large-scale production.

The invention has been exemplified by various specific embodiments. However, those of ordinary skill in the art can understand that the present invention is not limited to the specific embodiments. Those of ordinary skill in the art can make various changes or modifications within the scope of the present invention, and various technical features mentioned in various places in this specification can be combined with each other without departing from the spirit and scope of the present invention. Such modifications and variations are all within the scope of the present invention.

The invention claimed is:

1. A method for producing an antibody-drug conjugate intermediate by addition of acid, wherein the reaction scheme of the method is:

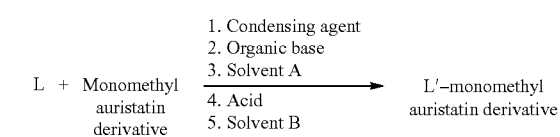

wherein
L is a linking group containing an acyl;
L' is the residue of the linking group covalently attached to the monomethyl auristatin derivative;
solvent A and solvent B are polar or non-polar solvents; and the method comprises the following steps:
1) dissolving the linking group L, the condensing agent, and the organic base in the solvent A to obtain solution 1;
2) dissolving the monomethyl auristatin derivative and the acid in the solvent B to obtain solution 2; and 3) adding the solution 1 into the solution 2 to obtain the L'-monomethyl auristatin derivative via the condensation reaction between L and the monomethyl auristatin derivative;

wherein the molar amount of the organic base used in step 1) is greater than the molar amount of all free carboxyl group in the reaction system of step 3);

L is

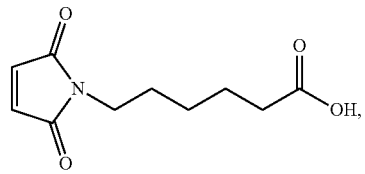 [SMILES: O=C(O)CCCCCN1C(=O)C=CC1=O]

the monomethyl auristatin derivative is MMAF, the condensing agent is HATU, the organic base is one or more selected from N,N-diisopropylethylamine and triethylamine, the solvent A and the solvent B are each independently selected from DMF, DMA and DMSO, the acid is one or more selected from trifluoroacetic acid, p-toluenesulfonic acid, trifluoromethanesulfonic acid, (−)-10-camphorsulfonic acid, (+)-10-camphorsulfonic acid and methanesulfonic acid, and the molar ratio of the acid to the monomethyl auristatin derivative is greater than 1.

2. The method according to claim 1, wherein the reaction scheme of the method is as follows:

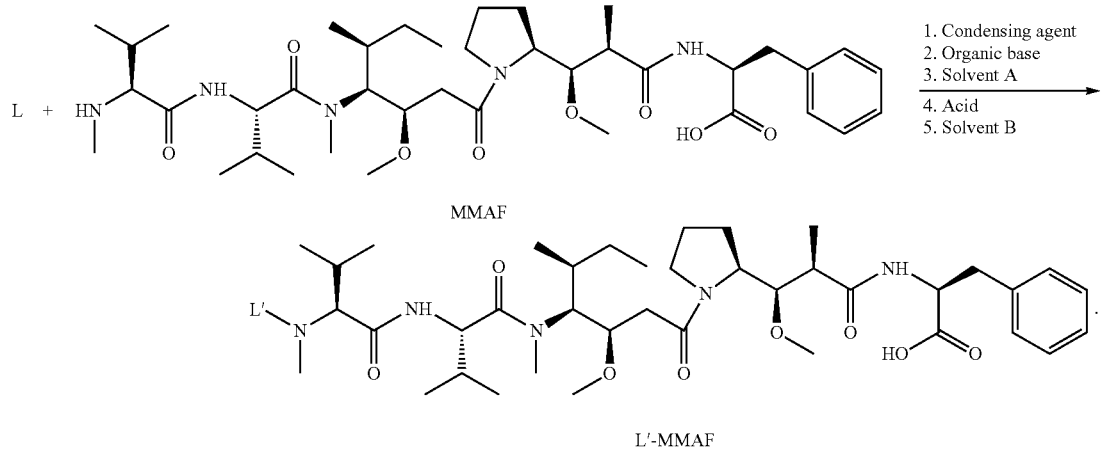

3. The method according to claim 2, wherein L'-MMAF is:

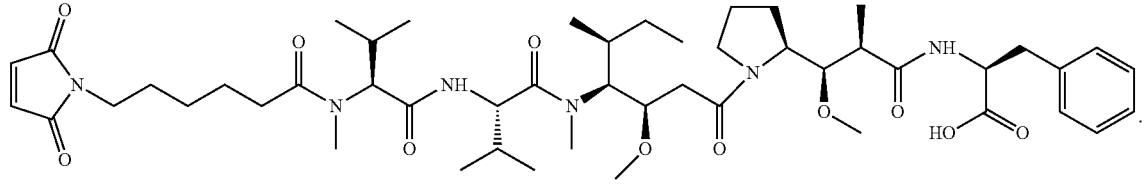 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)C(=O)CCCCCN1C(=O)C=CC1=O)C(C)C]

4. The method according to claim 1, wherein the solution 1 is added into solution 2 evenly.

5. The method according to claim 1, wherein the solution 1 is added into solution 2 by dropwise addition.

* * * * *